(12) United States Patent
Komatsubara

(10) Patent No.: US 11,213,014 B2
(45) Date of Patent: Jan. 4, 2022

(54) ABSORBENT ARTICLE FOR PETS

(71) Applicant: Unicharm Corporation, Ehime (JP)

(72) Inventor: Daisuke Komatsubara, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 471 days.

(21) Appl. No.: 16/311,030

(22) PCT Filed: Mar. 8, 2017

(86) PCT No.: PCT/JP2017/009303
§ 371 (c)(1),
(2) Date: Dec. 18, 2018

(87) PCT Pub. No.: WO2017/221472
PCT Pub. Date: Dec. 28, 2017

(65) Prior Publication Data
US 2019/0357499 A1 Nov. 28, 2019

(30) Foreign Application Priority Data

Jun. 22, 2016 (JP) .............................. JP2016-123984

(51) Int. Cl.
*A61F 13/514* (2006.01)
*A01K 23/00* (2006.01)
(Continued)

(52) U.S. Cl.
CPC ............ *A01K 23/00* (2013.01); *A61F 13/514* (2013.01); *A61D 9/00* (2013.01); *A61F 2013/15186* (2013.01)

(58) Field of Classification Search
CPC ....... A01K 23/00; A61D 9/00; A61F 13/4702; A61F 13/4704; A61F 13/49001;
(Continued)

(56) References Cited

U.S. PATENT DOCUMENTS

2006/0122570 A1* 6/2006 Kasai ................. A61F 13/532
604/385.24
2011/0209675 A1 9/2011 Esperon
(Continued)

FOREIGN PATENT DOCUMENTS

JP 1141707 U 9/1989
JP 2004141270 A 5/2004
(Continued)

OTHER PUBLICATIONS

English Abstract and Machine Translation for Japanese Publication No. 2012-187095 A, published Oct. 4, 2012, 15 pgs.
English Abstract and Machine Translation for Japanese Publication No. 2013-031380 A, published Feb. 14, 2013, 21 pgs.
English Abstract and Machine Translation for Japanese Publication No. 2012-161278 A, published Aug. 30, 2012, 25 pgs.
(Continued)

*Primary Examiner* — Catharine L Anderson
*Assistant Examiner* — Lynne Anderson
(74) *Attorney, Agent, or Firm* — Fredrikson & Byron, P.A.

(57) ABSTRACT

The purpose of the present invention is to provide an absorbent article for pets that fits the body of a pet in an excellent manner and is able to properly absorb liquid bodily waste such as urine. This absorbent article (1) for pets has mutually perpendicular longitudinal, width and thickness directions and is worn in such a way that the longitudinal direction extends around the body of a pet. The absorbent article (1) for pets comprises an absorbent body (4) that is provided with a deformation guide part (40) extending in a direction intersecting with the longitudinal direction in a plan view.

11 Claims, 10 Drawing Sheets

(51) Int. Cl.
*A61D 9/00* (2006.01)
*A61F 13/15* (2006.01)

(58) Field of Classification Search
CPC ............... A61F 13/532; A61F 13/5323; A61F 2013/15186; A61F 2013/4512; A61F 2013/4525; A61F 2013/5326
See application file for complete search history.

(56) References Cited

U.S. PATENT DOCUMENTS

| 2015/0045762 | A1 | 2/2015 | Komatsubara |
| 2017/0303512 | A1 | 10/2017 | Komatsubara |

FOREIGN PATENT DOCUMENTS

| JP | 2009254278 | A | 11/2009 |
| JP | 2012115464 | A | 6/2012 |
| JP | 2012143535 | A | 8/2012 |
| JP | 2012161278 | A | 8/2012 |
| JP | 2012187095 | A | 10/2012 |
| JP | 201331380 | A | 2/2013 |
| JP | 2013031380 | A | 2/2013 |
| JP | 5602973 | B1 | 10/2014 |
| WO | 2016075841 | A1 | 5/2016 |

OTHER PUBLICATIONS

English Abstract and Machine Translation for Japanese Publication No. 2012-143535 A, published Aug. 2, 2012, 16 pgs.
English Abstract for Japanese Publication No. 2004-141270 A, published May 20, 2004, 2 pgs.
English Machine Translation for Japanese Publication No. JPH01-141707 U, published Sep. 28, 1989, 3 pgs.
English Abstract and Machine Translation for Japanese Publication No. 2012-115464 A, published Jun. 21, 2012, 14 pgs.
English Abstract for Japanese Publication No. 2013-031380 A, published Feb. 14, 2013, 1 pg.
English Abstract for Japanese Publication No. 2012-161278 A, published Aug. 30, 2012, 1 pg.
English Abstract for Japanese Publication No. 2012-187095 A, published Oct. 4, 2012, 1 pg.
English Translation of PCT International Search Report from International Application No. PCT/JP2017/009303, dated Jun. 6, 2017, from which the instant application is based, 1 pg.
English Abstract and Machine Translation for Japanese Publication No. JP2009-254278A, published Nov. 5, 2009, 59 pgs.
English Abstract for Japanese Publication No. JP5602973B1, published Oct. 8, 2014, 1 pg.
Extended European Search Report dated May 7, 2019 for related European Patent Application No. 17814944.9, 8 pgs.

* cited by examiner

ABSORBENT ARTICLE FOR PETS

RELATED APPLICATIONS

This application is a 35 U.S.C. 371 national stage filing from international application No. PCT/JP2017/009303, filed Mar. 8, 2017, which claims priority to Japanese Application No. 2016-123984, filed Jun. 22, 2016, the teachings of which are incorporated herein by reference.

FIELD

The present invention relates to an absorbent article for pets, such as a disposable diaper, to be used for a pet such as a dog or cat.

BACKGROUND

Known absorbent articles for pets, for treatment of excreta that have been excreted by a pet such as a dog, include absorbent body-comprising belt-shaped disposable diapers that are worn by being wrapped around the torso of the pet.

An example of such a belt-shaped disposable diaper is disclosed in PTL 1, as a diaper for a pet to be worn by wrapping around the torso of the pet, such as male dog, comprising a belt-shaped top sheet having air permeability and liquid permeability, a belt-shaped back sheet having liquid impermeability, and an absorbent body disposed between these sheets and having a liquid-absorbing property, and comprising a standing part (three-dimensional gather) provided on the surface of the top sheet, along the lengthwise direction of the top sheet.

CITATION LIST

Patent Literature

[PTL 1] Japanese Unexamined Patent Publication No. 2012-187095

SUMMARY

Technical Problem

With the diaper for a pet disclosed in PTL 1, however, since the absorbent body that occupies most of the thickness of the diaper for a pet has an essentially constant thickness, when the diaper for a pet is worn by wrapping around the torso of the pet, the diaper for a pet curves at unintended locations, tending to form gaps between it and the torso of the pet, or causing the location of the diaper to shift from its proper position in the girth direction or in the front-rear direction of the pet. When gaps form between the diaper and the torso of the pet in this manner, or the diaper shifts from the proper position, such gap formation and the fact that the absorbent body can no longer match the site of urination (i.e. the urethral opening) of the pet, have made the absorbent body unable to properly absorb liquid excreta such as urine that have been discharged from the pet, and leakage to the outside has often occurred.

It is therefore an object of the present invention to provide an absorbent article for pets that has excellent fittability for the torso of the pet and can properly absorb liquid excreta such as urine.

Solution to Problem

One aspect (aspect 1) of the invention is an absorbent article for pets having a lengthwise direction, a widthwise direction and a thickness direction that are mutually perpendicular, and which is worn with the lengthwise direction extending around the torso of a pet, the absorbent article for pets including an absorbent body provided with a deformation guide part that extends in a direction intersecting with the lengthwise direction, in a plan view.

Since the absorbent article for pets of aspect 1 includes an absorbent body comprising a deformation guide part that extends in the direction intersecting with the lengthwise direction of the absorbent article (that is, the direction around the torso of the pet, when it is worn) in the plan view, when the absorbent article for pets is worn around the torso of the pet, the absorbent body easily bends along the torso of the pet due to the deformation guide part. As a result, the absorbent article for pets of this aspect is less likely to have gaps form between it and the torso of the pet, or to have the wearing position of the absorbent article for pets shift from the proper position.

Therefore, the absorbent article for pets of aspect 1 has excellent fittability for the torso of the pet and can properly absorb liquid excreta such as urine.

According to another aspect (aspect 2) of the invention, in the absorbent article for pets of aspect 1, the absorbent body has a lengthwise first region, a lengthwise center region and a lengthwise second region in that order, that divide the absorbent body into three equal portions in the lengthwise direction, in the plan view, the deformation guide part being disposed at least in the lengthwise center region.

Since the absorbent article for pets of aspect 2 has the deformation guide part of the absorbent body disposed in the lengthwise center region, the absorbent body easily bends along the excretory part (urethral opening) of a male pet so as to cover the excretory part, and when the absorbent article for pets is fitted onto the torso of the pet, the locations of the absorbent body and the pet excretory part are less likely to shift in the direction around the torso of the pet (that is, the locations of the absorbent body and the excretory part of the pet tend to match). Therefore, the absorbent article for pets of aspect 2 can more accurately absorb liquid excreta such as urine that have been discharged from a pet.

According to yet another aspect (aspect 3) of the invention, in the absorbent article for pets of aspect 1 or 2, the absorbent article for pets comprises an engagement section on at least one end in the lengthwise direction, and the absorbent body has a lengthwise first region, a lengthwise center region and a lengthwise second region in that order, that divide the absorbent body into three equal portions in the lengthwise direction, in the plan view, while the deformation guide part is disposed in either or both of the lengthwise first region and the lengthwise second region.

Since the absorbent article for pets of aspect 3 has the deformation guide part of the absorbent body disposed in either or both of the lengthwise first region and lengthwise second region, when the absorbent article for pets is worn around the torso of the pet, the absorbent article for pets can be fitted along the torso of the pet, while at least one end in the lengthwise direction of the absorbent article for pets can be engaged and fastened at the proper position. In addition, after the absorbent article for pets has been fitted onto the torso of the pet, the absorbent body is less likely to return from the state in which it is bent along the torso of the pet, to its original state (that is, the absorbent body is less likely to deform in a direction separating from the torso of the pet), and therefore the aforementioned engaged and fastened state is easily maintained, and there is a lower tendency for gaps to form between the absorbent article for pets and the torso of the pet, or for the absorbent article for pets to shift from the proper wearing position.

According to yet another aspect (aspect 4) of the invention, in the absorbent article for pets of any one of aspects 1 to 3, the absorbent body has a widthwise first region, a widthwise center region and a widthwise second region in that order, that divide the absorbent body into three equal portions in the widthwise direction in the plan view, the deformation guide part being disposed in either or both of the widthwise first region and the widthwise second region.

Since the absorbent article for pets of aspect 4 has the deformation guide part of the absorbent body disposed in either or both of the widthwise first region and the widthwise second region, the absorbent article for pets can be deformed to match the body shape of the pet and changes in the torso dimensions caused by movement such as respiration by the pet. That is, if the deformation guide part of the absorbent body is provided in the widthwise region which is at the rear side (i.e. the gluteal region side) of the pet when the absorbent article for pets is fitted onto the torso of the pet (for example, the widthwise second region), then when the absorbent article for pets is fitted onto the torso of the pet, the absorbent article for pets can be accurately fitted along the torso of the pet to match the torso dimension, which differs in the front-rear direction of the pet (that is, the widthwise direction of the absorbent article for pets) due to the body shape of the pet (the torso region of the pet on which the absorbent article for pets is worn will generally have a larger torso dimension (fatter torso) at the front and a smaller torso dimension (thinner torso) at the rear).

Moreover, if the deformation guide part of the absorbent body is provided in the widthwise region that is at the front side (i.e. the head side) of the pet when the absorbent article for pets is fitted onto the torso of the pet (for example, the widthwise first region), then when the absorbent article for pets is fitted onto the torso of the pet, the absorbent body, and therefore the absorbent article for pets, can deform following changes in the torso dimension in the front-rear direction of the pet caused by movement such as respiration by the pet, and the absorbent article for pets can satisfactorily maintain the closely fitted state onto the torso of the pet.

As a result, the absorbent article for pets of aspect 4 will have excellent fittability with the torso of the pet and will be less likely to shift from the proper wearing position (especially in the front-rear direction of the pet). Particularly when the absorbent article for pets of this aspect has the features of aspect 2 described above, the deformation guide part of the absorbent body can be situated to match the tip section of the excretory part of a male pet, so that when the absorbent article for pets is fitted onto the torso of the pet, the locations of the absorbent body and the excretory part of the pet are even less likely to shift in the direction around the torso of the pet, and liquid excreta discharged from the pet can be even more accurately absorbed.

According to yet another aspect (aspect 5) of the invention, in the absorbent article for pets of aspect 2 or 3, the absorbent body has a widthwise first region, a widthwise center region and a widthwise second region in that order, that divide the absorbent body into three equal portions in the widthwise direction in the plan view, the deformation guide part being disposed in the widthwise center region of the absorbent body.

Since the absorbent article for pets of aspect 5 has the deformation guide part of the absorbent body disposed in the widthwise center region, the absorbent article for pets easily bends in the widthwise center region to a convex shape toward the non-torso-facing side, and space able to accommodate liquid excreta discharged from the pet (excreta-accommodating space) can be formed locally (that is, in the widthwise center region) between the absorbent article for pets and the torso of the pet. This allows the absorbent article for pets of aspect 5 to hold liquid excreta in the excreta-accommodating space even when the pet has discharged a large amount of liquid excreta, thus more reliably preventing leakage of liquid excreta. In addition, if the deformation guide part of the absorbent body is disposed in the widthwise center region, the deformation guide part of the widthwise center region constitutes a bending origin, and the absorbent article for pets easily bends in the widthwise direction to a convex shape toward the non-torso-facing side, so that the widthwise first region and widthwise second region more easily fit in a close manner to the torso of the pet.

As a result, the absorbent article for pets of aspect 5 can more reliably prevent leakage of liquid excreta discharged from the pet, while also being even less likely to shift from the proper wearing position.

According to yet another aspect (aspect 6) of the invention, in the absorbent article for pets of any one of aspects 1 to 5, the absorbent article for pets comprises a freely stretchable center section elastic member extending in a direction intersecting with the widthwise direction and overlapping with the absorbent body in the thickness direction.

Since the absorbent article for pets of aspect 6 comprises a freely stretchable center section elastic member that extends in a direction intersecting with the widthwise direction and overlaps with the absorbent body in the thickness direction, both ends of the absorbent article for pets in the lengthwise direction are pulled in by the contractive force of the center section elastic member and easily fit along the torso of the pet. In addition, if it comprises such a center section elastic member, then even when the torso dimensions change due to movement such as respiration by the pet, the absorbent article for pets can match the change in torso dimensions to maintain a closely adhering state to the torso of the pet.

The absorbent article for pets of aspect 6 is therefore even less likely to have gaps form between it and the torso of the pet, and the absorbent article for pets is less likely to shift from the proper wearing position.

According to yet another aspect (aspect 7) of the invention, in the absorbent article for pets of aspect 6, the absorbent article for pets comprises, in the thickness direction, a liquid-permeable top sheet, a liquid-impermeable back sheet and the absorbent body situated between these sheets, the center section elastic member being disposed between the top sheet and the absorbent body.

Since the absorbent article for pets of aspect 7 has the center section elastic member disposed between the top sheet and absorbent body, the absorbent article for pets easily contracts to wrap around the torso of the pet due to contractive force of the center section elastic member, thus allowing more satisfactory fittability when it is worn. The absorbent article for pets of aspect 7 is thus yet even less likely to have gaps form between it and the torso of the pet, and the absorbent article for pets is less likely to shift from the proper wearing position.

If the center section elastic member is disposed between the top sheet and absorbent body, another advantage is provided since the center section elastic member will be easily visible through the top sheet, and therefore when the absorbent article for pets is fitted on the pet it can be easily fitted to the proper position using the center section elastic member as a mark.

According to yet another aspect (aspect 8) of the invention, in the absorbent article for pets of aspect 6, the absorbent article for pets comprises, in the thickness direction, a liquid-permeable top sheet, a liquid-impermeable back sheet and an absorbent body situated between these sheets, the center section elastic member being disposed between the back sheet and the absorbent body.

Since the absorbent article for pets of aspect 8 has the center section elastic member disposed between the back sheet and absorbent body, even when the absorbent body has swelled by absorbing liquid excreta discharged from the pet, the center section elastic member imparts contractive force for covering from the outer side of the swelled absorbent body (that is, from the back sheet side), and the closely fitted state of the absorbent article for pets onto the torso of the pet can be more reliably ensured. Thus, the absorbent article for pets of aspect 8 can be accurately fitted to the torso of the pet and is less likely to shift from the proper wearing position, even when the absorbent body has absorbed a fixed amount of liquid excreta.

Moreover, if the center section elastic member is disposed between the back sheet and absorbent body, then when an owner fits the absorbent article for pets onto a pet, the absorbent article for pets deforms to a convex shape on the top sheet side (that is, toward the torso-facing side) and the deformation guide part is easily visible through the top sheet, thus providing an advantage in that the owner can use the deformation guide part as a mark to easily fit the absorbent article for pets to the proper position.

According to yet another aspect (aspect 9) of the invention, in the absorbent article for pets of any one of aspects 1 to 8, the absorbent article for pets comprises freely stretchable side section elastic member extending in the lengthwise direction on each of both ends in the widthwise direction, in the plan view.

Since the absorbent article for pets of aspect 9 comprises freely stretchable side section elastic members extending in the lengthwise direction on each of both ends in the widthwise direction in the plan view, deformation of the deformation guide part is aided by contractive force of the side section elastic members, while both ends in the widthwise direction of the absorbent article for pets (i.e. the front-rear direction of the pet when it is worn) can also be more accurately fitted along the torso of the pet. The absorbent article for pets of aspect 9 can therefore even more reliably prevent leakage of liquid excreta discharged from the pet.

According to yet another aspect (aspect 10) of the invention, in the absorbent article for pets according to any one of aspects 1 to 9, the absorbent article for pets has a torso-facing surface that faces the torso of the pet and a non-torso-facing surface on an opposite side from the torso-facing surface, when it is fitted onto the torso of the pet, and in the thickness direction, the absorbent article comprises a liquid-permeable top sheet, a liquid-impermeable back sheet, the absorbent body situated between these sheets, and a freely stretchable surface-section elastic member located further to the torso-facing side than the top sheet and extending in the lengthwise direction.

Since the absorbent article for pets of aspect 10 comprises a freely stretchable surface-section elastic member located further to the torso-facing side than the absorbent body and extending in the lengthwise direction, deformation of the deformation guide part can be aided by contractive force of the surface-section elastic member, and it becomes easier to form anti-leakage walls running in the lengthwise direction between the top sheet and the torso of the pet. Thus, the absorbent article for pets of aspect 10 can even more reliably prevent leakage of liquid excreta discharged from the pet.

According to yet another aspect (aspect 11) of the invention, in the absorbent article for pets according to any one of aspects 1 to 10, the absorbent body has different rigidity for the deformation guide part and for at least one neighboring regions of two neighboring regions adjacent to both sides of the deformation guide part, in the direction in which the deformation guide part extends in the plan view.

Since the absorbent body of the absorbent article for pets of aspect 11 has different rigidity for the deformation guide part and for the neighboring regions of the deformation guide part, thus being constructed with border sections having different rigidities serving as bending origins and making the absorbent body easier to bend, it is possible to ensure the function of the deformation guide part and to ensure consistent absorption performance. Thus, the absorbent article for pets of aspect 11 can ensure excellent fittability with the torso of the pet, and can more accurately absorb liquid excreta such as urine.

Moreover, since the absorbent article for pets of aspect 11 allows the deformation guide part to be constructed by a difference in rigidity in the absorbent body, an advantage is provided in that the ease of deformation, the direction of deformation and the manner of deformation of the deformation guide part can be easily controlled, and more accurate fittability can be exhibited to match the body shape of the pet.

Advantageous Effects of Invention

According to the invention it is possible to provide an absorbent article for pets that has excellent fittability for the torso of the pet and can properly absorb liquid excreta such as urine.

DESCRIPTION OF EMBODIMENTS

Figure 1:
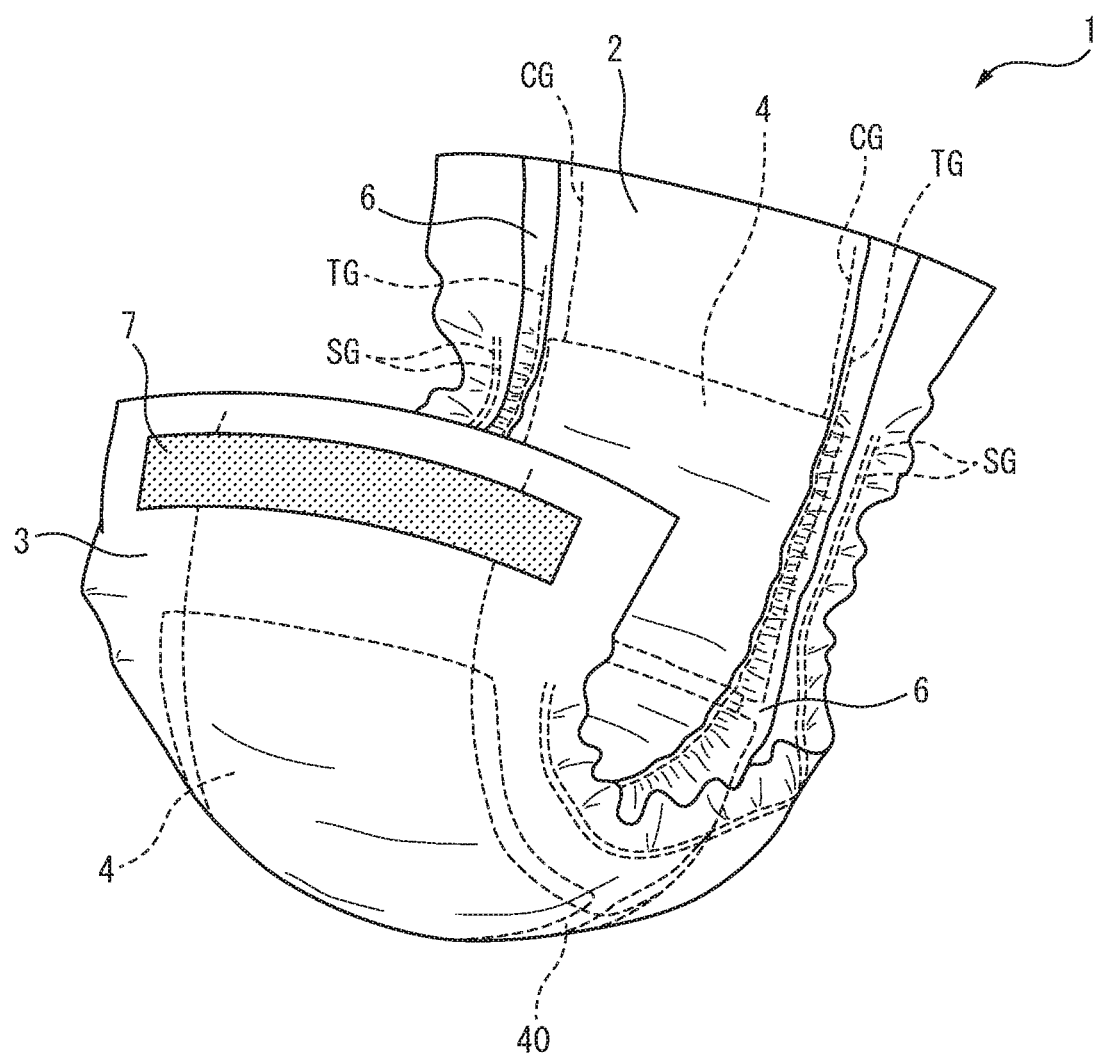
FIG. 1 is a perspective view of a diaper for a pet 1, according to a first embodiment of the invention.

Preferred embodiments of the absorbent article for pets of the invention will now be explained in greater detail with reference to the accompanying drawings. Throughout the present specification, unless otherwise specified, the concept of "viewing an object (for example, an absorbent article or absorbent body) on the horizontal plane in the expanded state in the thickness direction of the object, from the upper side in the vertical direction", will be referred to by the phrase "in the plan view". When the object is an absorbent article, in particular, viewing the absorbent article in the expanded state from the top sheet side in the thickness direction may referred to simply as "the plan view".

The directions used throughout the present specification are as follows, unless otherwise specified.

Throughout the present specification, "lengthwise direction" refers to the "long direction among the lengths of a longitudinal object in the plan view", "widthwise direction" refers to the "short direction among the lengths of a longitudinal object in the plan view", and "thickness direction" refers to the "vertical direction of an object situated on the horizontal plane in the expanded state". The lengthwise direction, widthwise direction and thickness direction are in a mutually perpendicular relationship.

Also, throughout the present specification, the concept of the "relatively proximal side in the widthwise direction of a longitudinal object (for example, an absorbent article or absorbent body), with respect to a widthwise center axis line running in the lengthwise direction" will be referred to as the "inner side in the widthwise direction", and the concept of the "relatively distal side in the widthwise direction of a longitudinal object, with respect to a widthwise center axis line running in the lengthwise direction" will be referred to as the "outer side in the widthwise direction".

Also throughout the present specification, the concept of "one side that is to be the relatively proximal side with respect to the head of the pet, in the direction of extension of the torso of the pet on which the absorbent article is to be fitted" will be referred to as the "front side of the pet", and the concept of "the other side that is to be the relatively distal side with respect to the head of the pet in the direction of extension of the torso of the pet on which the absorbent article is to be fitted (i.e. the relatively proximal side with respect to the gluteal region of the pet)" will be referred to as the "rear side of the pet". Throughout the present specification, the phrases "direction toward the front side of the pet" and "direction toward the rear side of the pet" may be referred to as the "front of the pet" and the "rear of the pet", respectively.

Also throughout the present specification, unless otherwise specified, the "one side that is to be the relatively proximal side with respect to the torso of the pet when the absorbent article has been fitted onto the torso of the pet, in the thickness direction of the absorbent article" will be referred to as the "torso-facing side", and the "one side that is to be the relatively distal side with respect to the torso of the pet when the absorbent article has been fitted onto the torso of the pet, in the thickness direction of the absorbent article" will be referred to as the "non-torso-facing side". Incidentally, throughout the present specification, the "surface on the torso-facing side" and "surface on the non-torso-facing side" for each of the members composing the absorbent article (for example, the top sheet, absorbent body, back sheet and back film) will be referred to simply as "torso-facing surface" and "non-torso-facing surface", respectively. The "torso-facing surface" and the "non-torso-facing surface" are surfaces on mutually opposite sides.

First Embodiment

Figure 2:
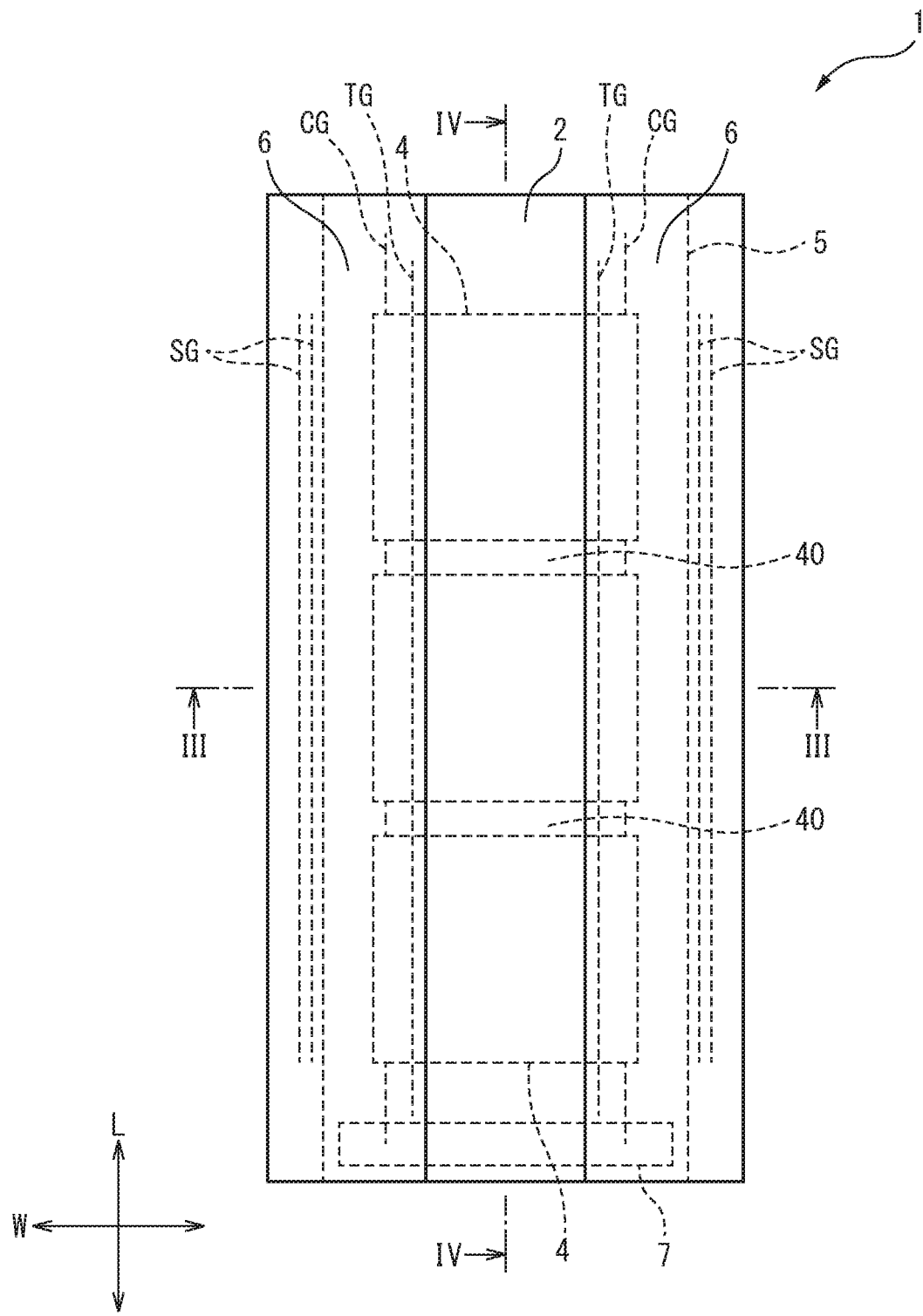
FIG. 2 is a plan view of the diaper for a pet 1, in the expanded state.
Figure 3:
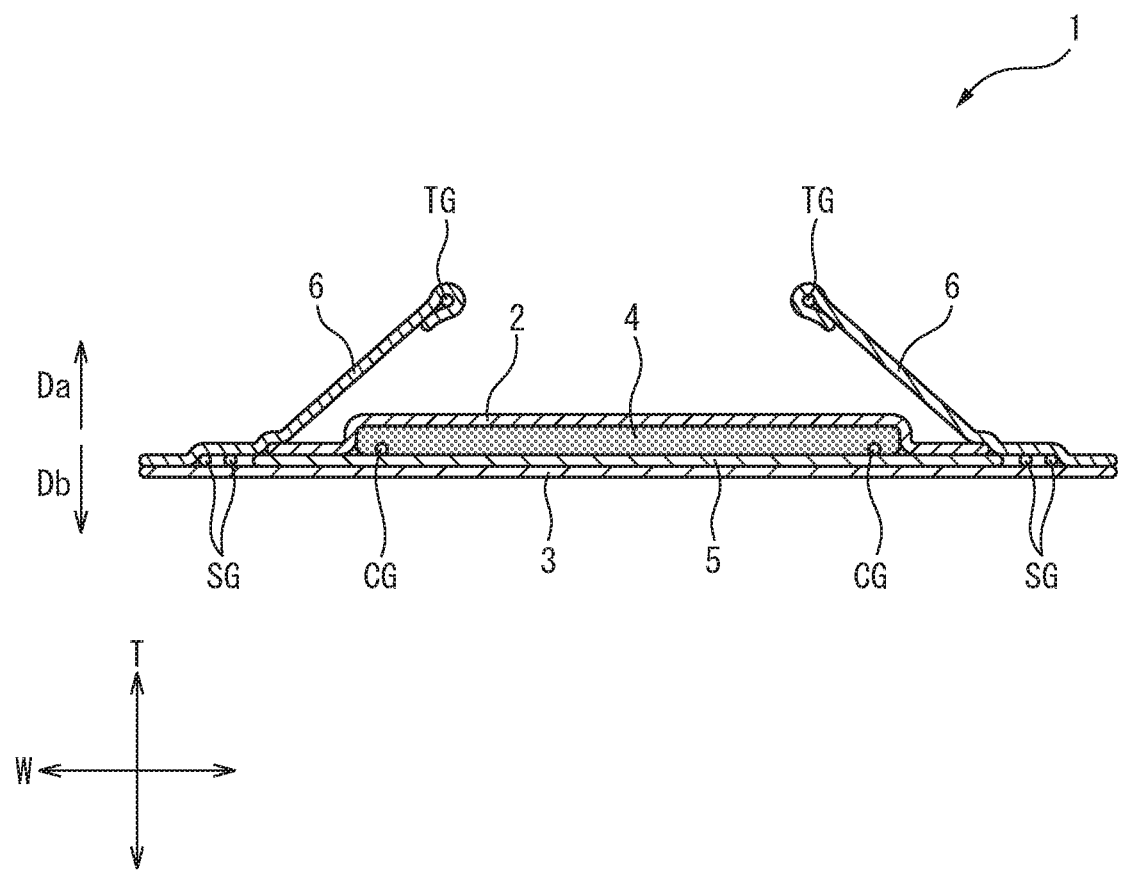
FIG. 3 is a widthwise cross-sectional end view of the diaper for a pet 1 along line III-III of FIG. 2.
Figure 4:
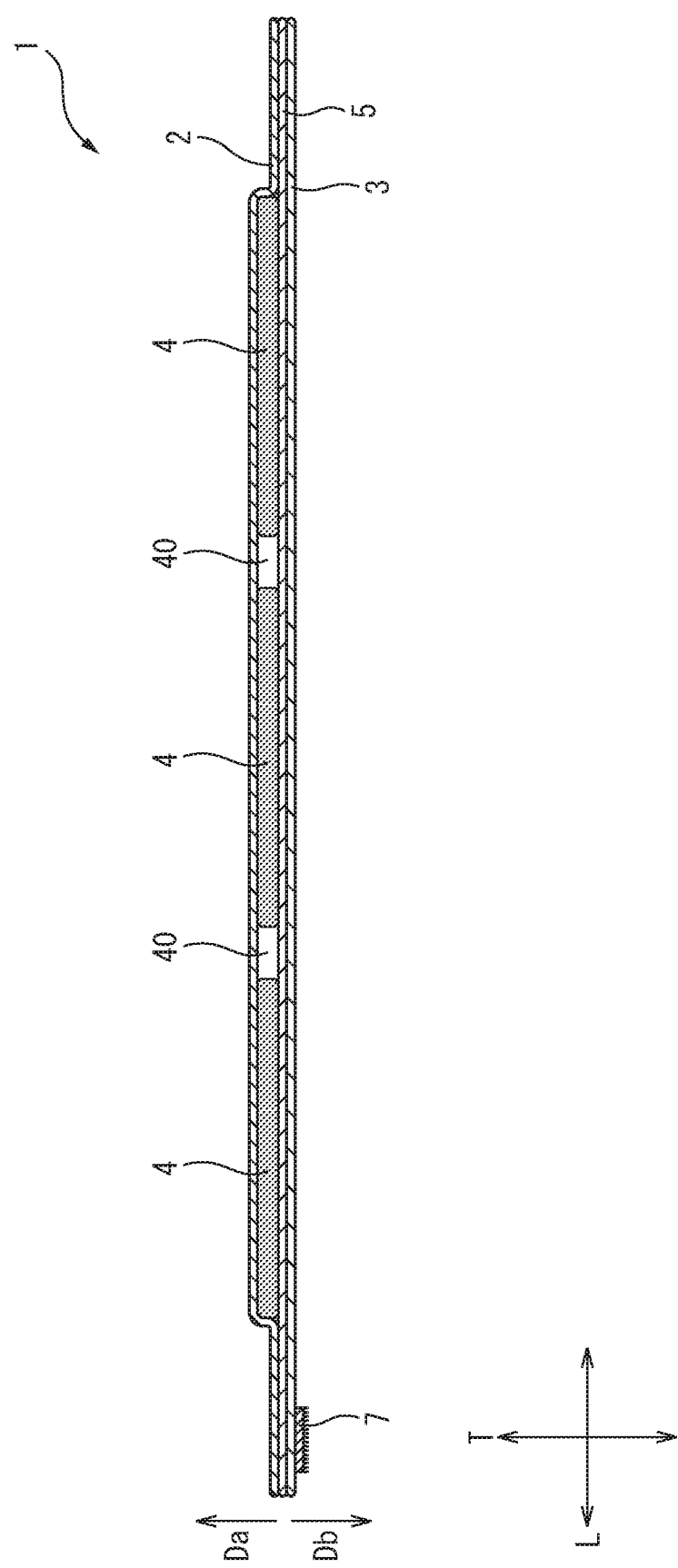
FIG. 4 is a lengthwise cross-sectional end view of the diaper for a pet 1 along line IV-IV of FIG. 2.

FIG. 1 is a perspective view of a diaper for a pet 1 according to a first embodiment of the invention, and FIG. 2 is a plan view of the diaper for a pet 1 in the expanded state. FIG. 3 is a widthwise cross-sectional end view of the diaper for a pet 1 along line III-III of FIG. 2, and FIG. 4 is a lengthwise cross-sectional end view of the diaper for a pet 1 along line IV-IV of FIG. 2.

As shown in FIG. 1 and FIG. 2, the diaper for a pet 1 according to the first embodiment of the invention has a longitudinal outer shape (specifically a rectangular outer shape) having a lengthwise direction L and widthwise direction W, in the plan view, and is constructed so that its lengthwise direction L is to wrap around the torso of the pet, matching the direction of the torso that includes the dorsal region and abdominal region of the pet (the girth direction).

According to the invention, the outer shape and outer dimensions of the absorbent article for pets are not limited to this type of outer shape, and so long as it is a long shape having a length in the lengthwise direction that is longer than the length around the torso of the pet, any desired longitudinal outer shape (for example, rectangular, elliptical or gourd-shaped) and outer dimensions may be employed, depending on the type, body frame and size of the pet.

As shown in FIGS. 1 to 4, the diaper for a pet 1 has a basic construction comprising, in the thickness direction T, a liquid-permeable top sheet 2 situated on the torso-facing side Da, a liquid-impermeable back sheet 3 situated on the non-torso-facing side Db, and an absorbent body 4 disposed between these sheets and comprising two slits 40 (deformation guide parts) that extend in the widthwise direction W (the direction that is to be the front-rear direction of the pet when it is worn) which is orthogonal to the lengthwise direction L of the diaper for a pet 1 (the direction that is to be the direction around the torso of the pet when it is worn), the diaper being constructed so that liquid excreta such as urine that have been discharged from the pet can be absorbed and held in the absorbent body 4 while permeating through in the thickness direction T.

Also, the diaper for a pet 1 comprises a back film 5 disposed between the absorbent body 4 and back sheet 3, a pair of side sheets 6 disposed on either side of the widthwise center axis line running in the lengthwise direction L of the diaper for a pet 1, on the torso-facing side Da of the top sheet 2, and an engagement section 7 disposed on one end in the lengthwise direction L of the diaper for a pet 1, on the non-torso-facing surface of the back sheet 3, the construction being such that the diaper for a pet 1 can be fitted in a steady manner onto the torso of the pet, and liquid excreta such as urine that have been discharged from the pet are unlikely to leak to the outside.

Incidentally, of the aforementioned members composing the diaper for a pet 1, the absorbent body 4 is disposed in the center region that includes the widthwise center axis line running in the lengthwise direction L of the diaper for a pet 1 in the plan view, extending along a wide area in the lengthwise direction L of the diaper for a pet 1, and the top sheet 2 and back sheet 3 are disposed extending from the edge on one side to the edge on the other side in the lengthwise direction L of the diaper for a pet 1, so as to cover the absorbent body 4 from both sides, the torso-facing side and the non-torso-facing side.

As shown in FIGS. 1 to 3, the diaper for a pet 1 of the first embodiment further comprises a pair of center section elastic members CG that are freely stretchable in the lengthwise direction L, respectively situated at locations overlapping in the thickness direction T with both ends in the widthwise direction W of the absorbent body 4 and extending in the lengthwise direction L, between the back sheet 3 and absorbent body 4, side section elastic members SG that are freely stretchable in the lengthwise direction L, respectively situated at locations of both ends in the widthwise direction W of the diaper for a pet 1 and extending in the lengthwise direction L, between the side sheets 6 and back sheet 3, and a pair of surface-section elastic members TG that are freely stretchable in the lengthwise direction L, respectively situated at the inner side ends in the widthwise direction W of the pair of side sheets 6 located on the torso-facing side Da of the top sheet 2, and extending in the lengthwise direction L.

The functions of each of these elastic members will be described below, but since the diaper for a pet 1 is stretchable in the lengthwise direction L due to these elastic members, when the diaper for a pet 1 is fitted onto the torso of the pet, the circumference of the diaper for a pet 1 along the direction around the torso of the pet (that is, the length in the lengthwise direction in the plan view) contracts, allowing the diaper for a pet 1 to easily fit to match the body shape of the pet. Moreover, since the diaper for a pet 1 that has been fitted onto the torso of the pet is stretchable in the direction around the torso of the pet (that is, the lengthwise direction L in the plan view) to conform to changes in the torso dimension that occur with movement such as respiration by the pet, the diaper for a pet 1 easily maintains a closely fitted state with the torso of the pet for prolonged periods.

The engagement section 7 is composed of a mechanical fastener comprising a belt-shaped base joined to the non-torso-facing surface of the back sheet 3 and a plurality of hook members protruding from the base to the non-torso-facing side Db, and when the diaper for a pet 1 is fitted along the torso from the abdominal region side of the pet, the hook members can be engaged with any portion of the torso-facing surface of the top sheet 2 on the dorsal region side of the pet. By having such an engagement section 7, the diaper for a pet 1 can be accurately fitted at the proper location of the torso of the pet, matching the dimensions of the torso of the pet.

Moreover, as shown in FIG. 1, FIG. 2 and FIG. 4, the absorbent body 4 in the diaper for a pet 1 of the first embodiment comprises deformation guide parts formed by two slits 40 extending in the widthwise direction W in the plan view. The slits 40 forming the deformation guide parts are cut sections running through the absorbent body 4 in the thickness direction T, and they have a direction in which the slits 40 run (that is, the lengthwise direction of the slits 40) and a direction perpendicular to that direction (that is, the widthwise direction of the slits 40). For the first embodiment, the lengthwise direction of the slits is parallel to the widthwise direction W of the diaper for a pet 1.

For the first embodiment, as shown in FIG. 2, the slits 40 forming the deformation guide parts extend from one edge across to the other edge in the widthwise direction W of the absorbent body 4, and therefore the absorbent body 4 is present inside the diaper for a pet 1 in a state divided into three parts in the lengthwise direction L, due to the two slits 40. Incidentally, as explained below, the structures of the slits are not an essential constituent feature of the invention, and the slits do not need to extend from one edge to the other edge in the widthwise direction of the absorbent body (that is, they may extend only partially in the widthwise direction of the absorbent body), and they do not need to run through the thickness direction of the absorbent body (that is, they may be formed as recesses that do not run through the thickness direction of the absorbent body (more specifically, recesses depressed from the torso-facing side and/or recesses depressed from the non-torso-facing side)).

Figure 5:
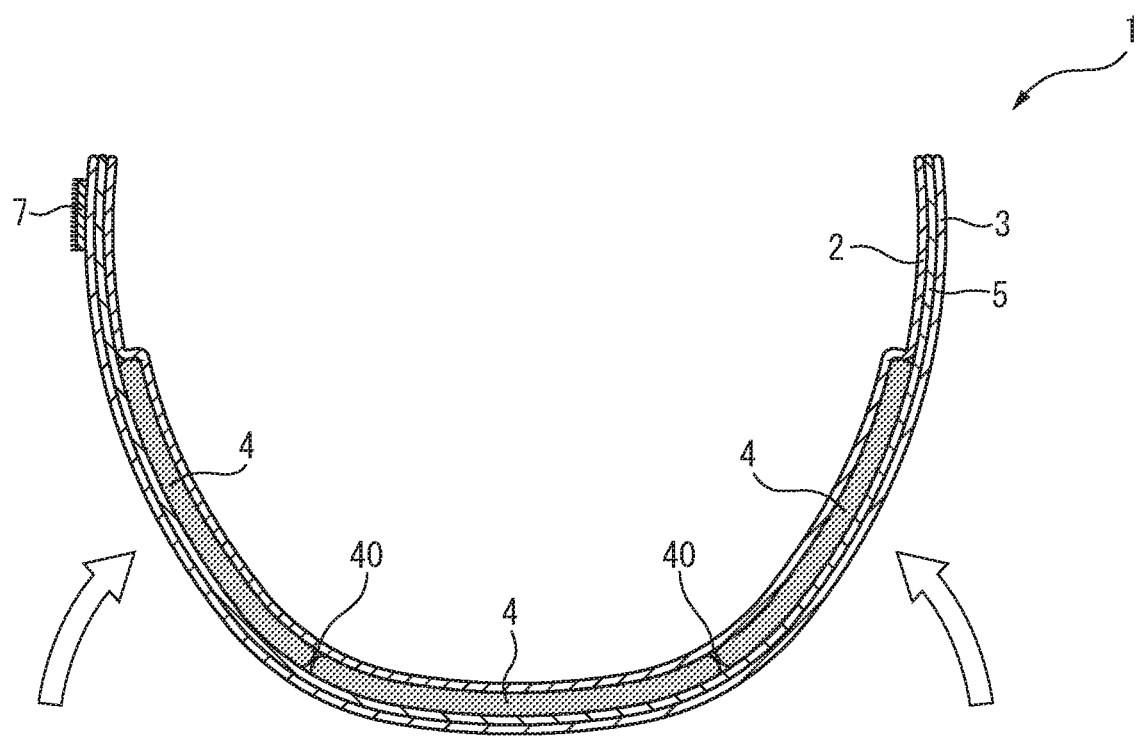
FIG. 5 is a lengthwise cross-sectional end view schematically showing a condition where the diaper for a pet 1 bends to the torso-facing side.

FIG. 5 is a lengthwise cross-sectional end view schematically showing a condition where the diaper for a pet 1 bends to the torso-facing side Da.

Since the diaper for a pet 1 of the first embodiment includes the absorbent body 4 provided with deformation guide parts comprising two slits 40 extending in the widthwise direction W in the plan view (an example of the "direction intersecting with the lengthwise direction of the absorbent article" according to the invention), when the diaper for a pet 1 is fitted onto the torso of the pet, as shown in FIG. 5, the absorbent body 4 easily bends along the torso of the pet due to the deformation guide parts (more specifically, the deformation guide parts serve as bending origins). As a result, the diaper for a pet 1 is less likely to have gaps form between it and the torso of the pet, or to have the wearing position of the absorbent article for pets shift from the proper position.

Therefore, the diaper for a pet 1 of the first embodiment has excellent fittability for the torso of the pet and can properly absorb liquid excreta such as urine.

Figure 6:
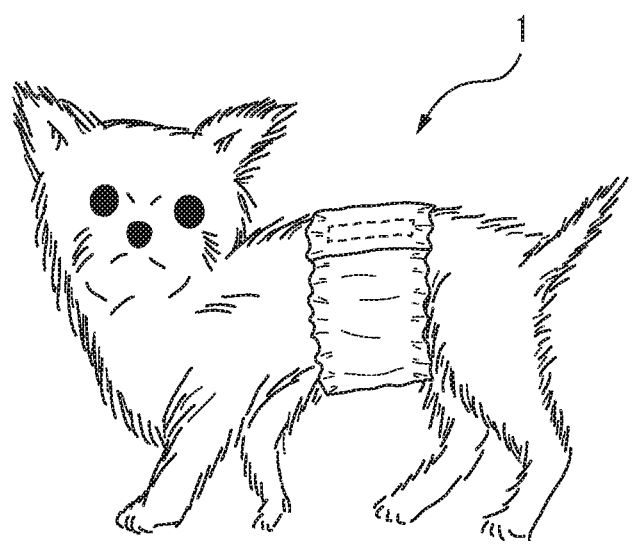
FIG. 6 is a schematic diagram showing the diaper for a pet 1 when fitted onto a dog.

The diaper for a pet 1 of the first embodiment is fitted onto the torso of the pet in the following manner. FIG. 6 is a schematic diagram showing the state of the diaper for a pet 1 when fitted onto a dog (an example of a "pet").

First, the diaper for a pet 1 is applied to the abdominal region of the pet with the lengthwise direction L intersecting with the front-rear direction of the pet (that is, the widthwise direction W matches the front-rear direction of the pet) and the absorbent body 4 facing the excretory part (urethral opening) of the pet. The diaper for a pet 1 that has been applied to the abdominal region of the pet is then wrapped around the torso of the pet, from the abdominal region along the torso. At the dorsal region of the pet during this time, one end in the lengthwise direction L of the diaper for a pet 1 overlaps with the top of the other end (on the non-torso-facing surface), and at that end it is engaged and fastened by the engagement section 7 disposed on the non-torso-facing surface of the back sheet 3. The diaper for a pet 1 is thus fitted onto the torso of the pet as shown in FIG. 6.

The "pet" to which the absorbent article for pets of the invention is to be applied is an animal that can be reared as a pet, and it is not particularly restricted so long as it is a "male" animal such as a male dog, which has its excretory part (urethral opening) located on the underbelly, and it may be one of various species of animals other than dogs (male dogs), such as cats and monkeys.

The "liquid excreta" to be absorbed and held by the absorbent article for pets of the invention are not particularly restricted so long as they can be absorbed and held in the absorbent body described below, and for example, they may be various types of liquid to low-viscosity body fluids such as urine or blood.

Each of the members of the absorbent article for pets of the invention will now be explained in detail using the diaper for a pet 1 of the first embodiment.

Top Sheet

As shown in FIGS. 2 to 4, the top sheet 2 in the diaper for a pet 1 of the first embodiment of the invention has a longitudinal rectangular outer shape extending in the lengthwise direction L and widthwise direction W of the diaper for a pet 1, in the plan view, and it is composed of a liquid-permeable sheet member, disposed on the torso-facing side Da in the thickness direction T of the diaper for a pet 1, that may directly contact the body of the pet to which it is fitted. According to the invention, the liquid-permeable sheet member is not particularly restricted so long as it has properties allowing it to be used as a top sheet for an absorbent article for pets (for example, liquid permeability and flexibility), and for example, any desired nonwoven fabric may be used, such as a spunlace nonwoven fabric, air-through nonwoven fabric, spunbond nonwoven fabric, point bonded nonwoven fabric or meltblown nonwoven fabric, or a combination thereof (for example, an SMS nonwoven fabric). The structure of the nonwoven fabric to be used as the top sheet is also not particularly restricted, and it may be a flat, nonporous nonwoven fabric, or it may be a perforated nonwoven fabric or a nonwoven fabric having a concavoconvex structure (a concavoconvex structure or ridge-groove structure with an undulating cross-sectional shape). The type of fibers used in the nonwoven fabric is also not particularly restricted, and examples include cellulosic fibers; and hydrophilic fibers such as hydrophilicized thermoplastic resin fibers of an olefin-based resin or polyester-based resin, any of which may be used alone or in combinations of two of more different types of fibers.

According to the invention, the dimensional shape of the top sheet is not particularly restricted so long as it can cover the torso-facing surface of the absorbent body, and any desired dimensional shape may be employed which is suited for the size and body frame of the animal that is to be fitted with the absorbent article for pets. The basis weight of the top sheet is also not particularly restricted so long as the effect of the invention is not inhibited, and for example, a basis weight in the range of 5 $g/m^2$ to 100 $g/m^2$ may be employed, but a basis weight in the range of 6 $g/m^2$ to 50 $g/m^2$ is preferred from the viewpoint of liquid-permeability and flexibility. The basis weight can be measured according to JIS L 1906 5.2.

The thickness of the top sheet is also not particularly restricted so long as the effect of the invention is not inhibited, and for example, a thickness in the range of 0.001 mm to 5.0 mm may be employed, although a thickness in the range of 0.01 mm to 3.0 mm is preferred and a thickness in the range of 0.1 mm to 1.0 mm is more preferred from the viewpoint of liquid-permeability and flexibility.

The thicknesses of the sheet members such as the top sheet can be determined by the following measuring method.

Method of Measuring Sheet Member Thickness (1) A sample sheet of a prescribed size (for example, 100 mm×100 mm) is cut out from the sheet member to be measured.

(2) The cut out sample sheet is set in an automated compression tester "KES FB-3A" by Kato Tech Corp., the thickness (mm) is measured with a pressure of 49 Pa on the sample sheet by the measuring terminal of the tester, and the thickness (mm) is recorded as the thickness of the sample sheet.

Back Sheet

As shown in FIGS. 2 to 4, the back sheet 3 of the diaper for a pet 1 of the first embodiment of the invention has a longitudinal rectangular outer shape extending in the lengthwise direction L and widthwise direction W of the diaper for a pet 1, in the plan view, and it is composed of a liquid-impermeable sheet member, disposed on the non-torso-facing side Db in the thickness direction T of the diaper for a pet 1, that prevents leakage of liquid excreta such as urine that have been discharged from the pet on which the diaper is fitted. According to the invention, the liquid-impermeable sheet member is not particularly restricted so long as it has properties (for example, liquid impermeability, air permeability and flexibility) allowing it to be used as a back sheet for an absorbent article for pets, and for example, a hydrophobic nonwoven fabric, SMS layered nonwoven fabric, liquid-impermeable plastic film, or a laminated sheet comprising any desired combination of these sheets, may be used.

According to the invention, the dimensional shape of the back sheet is not particularly restricted so long as it can cover the non-torso-facing surface of the absorbent body and can prevent leakage of liquid excreta discharged from the pet on which it is fitted, and any desired dimensional shape may be employed which is suited for the size and body frame of the animal that is to be fitted with it. The thickness of the back sheet is also not particularly restricted so long as the effect of the invention is not inhibited, and for example, a thickness in the range of 0.001 mm to 5.0 mm may be employed, although a thickness in the range of 0.003 mm to 3.0 mm is preferred and a thickness in the range of 0.01 mm to 1.0 mm is more preferred from the viewpoint of liquid impermeability, flexibility and air permeability.

Absorbent Body

As shown in FIGS. 2 to 4, the absorbent body 4 of the diaper for a pet 1 of the first embodiment of the invention has a longitudinal rectangular outer shape extending overall in the lengthwise direction L and widthwise direction W of the diaper for a pet 1, in the plan view, and it is composed of a water absorbing member that is disposed between the top sheet 2 and back sheet 3 in the thickness direction T of the diaper for a pet 1, and that absorbs and holds liquid excreta such as urine of the pet, which have permeated the top sheet 2. As shown in FIG. 2, the absorbent body 4 is disposed so that it extends straddling the lengthwise center axis line (not shown) running in the widthwise direction W and extends straddling the widthwise center axis line (not shown) running in the lengthwise direction L of the diaper for a pet 1, in the plan view. According to the invention, the outer shape of the absorbent body as a whole in the plan view is not limited to such a rectangular shape, and so long as the shape is a longitudinal shape such that the length dimension is longer in the lengthwise direction L than in the widthwise direction W, any longitudinal shape (for example, hourglass-shaped or elliptical) may be employed, depending on the particular body frame of the animal.

The water absorbing member composing the absorbent body of the invention is not particularly restricted so long as it absorbs and holds liquid excreta such as urine that have been discharged from the pet and comprises deformation guide parts such as slits, and any water absorbing member known in the relevant field may be used. Examples of such water absorbing members include absorbent cores made of absorbent materials containing water-absorbent fibers such a pulp and/or a superabsorbent polymer, that are covered by at least one liquid-permeable cover sheet such as a tissue that is hydrophilic.

Moreover, as shown in FIG. 2 and FIG. 4, the absorbent body 4 in the diaper for a pet 1 comprises deformation guide parts formed by two slits 40 extending in the widthwise direction W in the plan view. The two slits 40 composing the deformation guide parts run through the absorbent body 4 in the thickness direction T, and extend from one edge across to the other edge in the widthwise direction W of the absorbent body 4. The absorbent body 4 is therefore disposed inside the diaper for a pet 1 in a state divided into three parts in the lengthwise direction L by the two slits 40.

If the absorbent body 4 thus comprises deformation guide parts (that is, two slits 40) extending in the widthwise direction W that is orthogonal to the lengthwise direction L of the diaper for a pet 1 (that is, the direction corresponding to the direction around the torso of the pet when the diaper for a pet 1 is worn) in the plan view, then when the diaper for a pet 1 is fitted onto the torso of the pet, the absorbent body 4 will easily bend in the lengthwise direction L along the torso of the pet due to the deformation guide parts extending in the widthwise direction W (see FIG. 5), and therefore the diaper for a pet 1 including the absorbent body 4 will be less likely to have a gap formed between it and the torso of the pet or to have the wearing position of the diaper for a pet 1 shift from the proper position. Therefore, the diaper for a pet 1 will have excellent fittability for the torso of the pet and will be able to properly absorb liquid excreta such as urine.

According to the invention, the direction of extension of the deformation guide part is not limited to the widthwise direction of the first embodiment so long as it is a direction intersecting with the lengthwise direction of the absorbent article for pets in the plan view, and any direction may be employed, depending on the type and body frame of the pet.

Throughout the present specification, the "direction intersecting with a prescribed direction (for example, the lengthwise direction or widthwise direction of the absorbent article for pets)" means the "direction such that the angle formed with the prescribed direction is in a range of from 45° to 90° (for example, the widthwise direction or lengthwise direction of the absorbent article for pets)". Therefore, a direction intersecting with the lengthwise direction is a direction such that the angle formed with the lengthwise direction is from 45° to 90°.

The aspect of the deformation guide parts for the absorbent article for pets of the invention is not limited to that of the first embodiment so long as the effect of the invention is not inhibited, and any aspect may be employed, depending on the type and body frame of the pet.

The aspects of the deformation guide parts that may be employed in the absorbent article for pets of the invention will now be described in detail, using different embodiments from the first embodiment (that is, the second embodiment to fifth embodiment) as examples. Since the construction other than the parts differing from the first embodiment described above are basically the same as the construction of the first embodiment described above, they will not be explained again.

Second Embodiment

Figure 7:
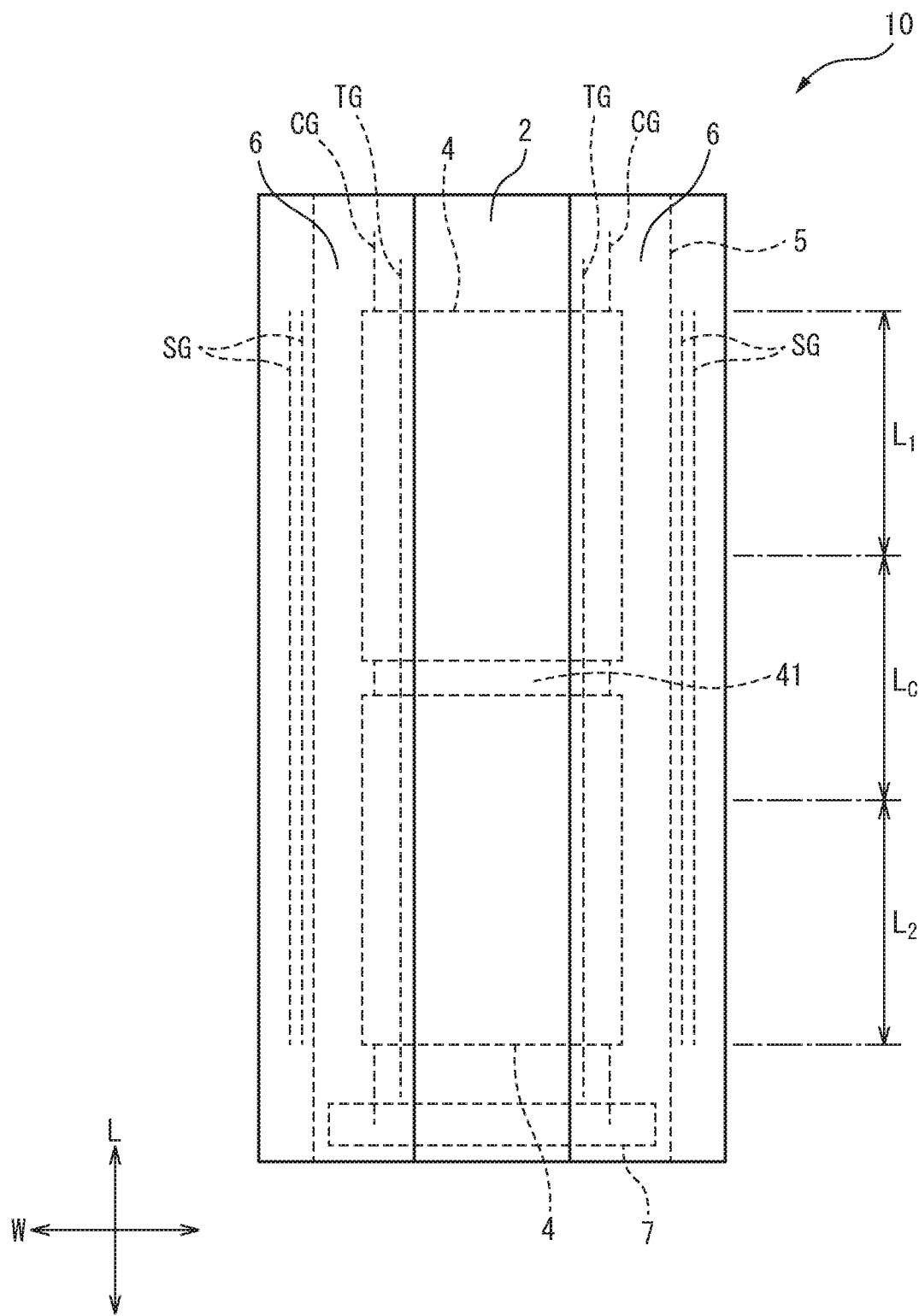
FIG. 7 is a plan view of the expanded state of a diaper for a pet 10 according to a second embodiment of the invention.

FIG. 7 is a plan view of the expanded state of a diaper for a pet 10 according to a second embodiment of the invention. In the diaper for a pet 10 of the second embodiment, as shown in FIG. 7, the absorbent body 4 has a lengthwise first region $L_1$, a lengthwise center region $L_C$ and a lengthwise second region $L_2$ in that order, that divide the absorbent body 4 into three equal portions in the lengthwise direction L in the plan view, and the deformation guide part formed by a single slit 41 extending in the widthwise direction W of the diaper for a pet 10 is situated in the lengthwise center region $L_C$. The single slit 41 forming this deformation guide part runs through the absorbent body 4 in the thickness direction T, and extends from one edge across to the other edge in the widthwise direction W of the absorbent body 4. The absorbent body 4 is therefore disposed inside the diaper for a pet 10 in a state divided into two parts in the lengthwise direction L by the single slit 41.

For the second embodiment, the deformation guide part is situated only in the lengthwise center region $L_C$, but according to the invention there is no limitation to this arrangement, and the deformation guide part may also be similarly arranged in a lengthwise region other than the lengthwise center region $L_C$ (that is, either or both the lengthwise first region $L_1$ and lengthwise second region $L_2$). When the deformation guide part of the absorbent body 4 is thus arranged at least in the lengthwise center region $L_C$, the absorbent body 4 easily bends along the excretory part of a male pet to cover the excretory part, and when the diaper for a pet 10 has been fitted onto the torso of the pet, the positions of the absorbent body 4 and the excretory part of the pet are less likely to shift in the direction around the torso of the pet. Thus, the diaper for a pet 10 of the second embodiment can more accurately absorb liquid excreta such as urine that have been discharged from a pet.

Third Embodiment

Figure 8:
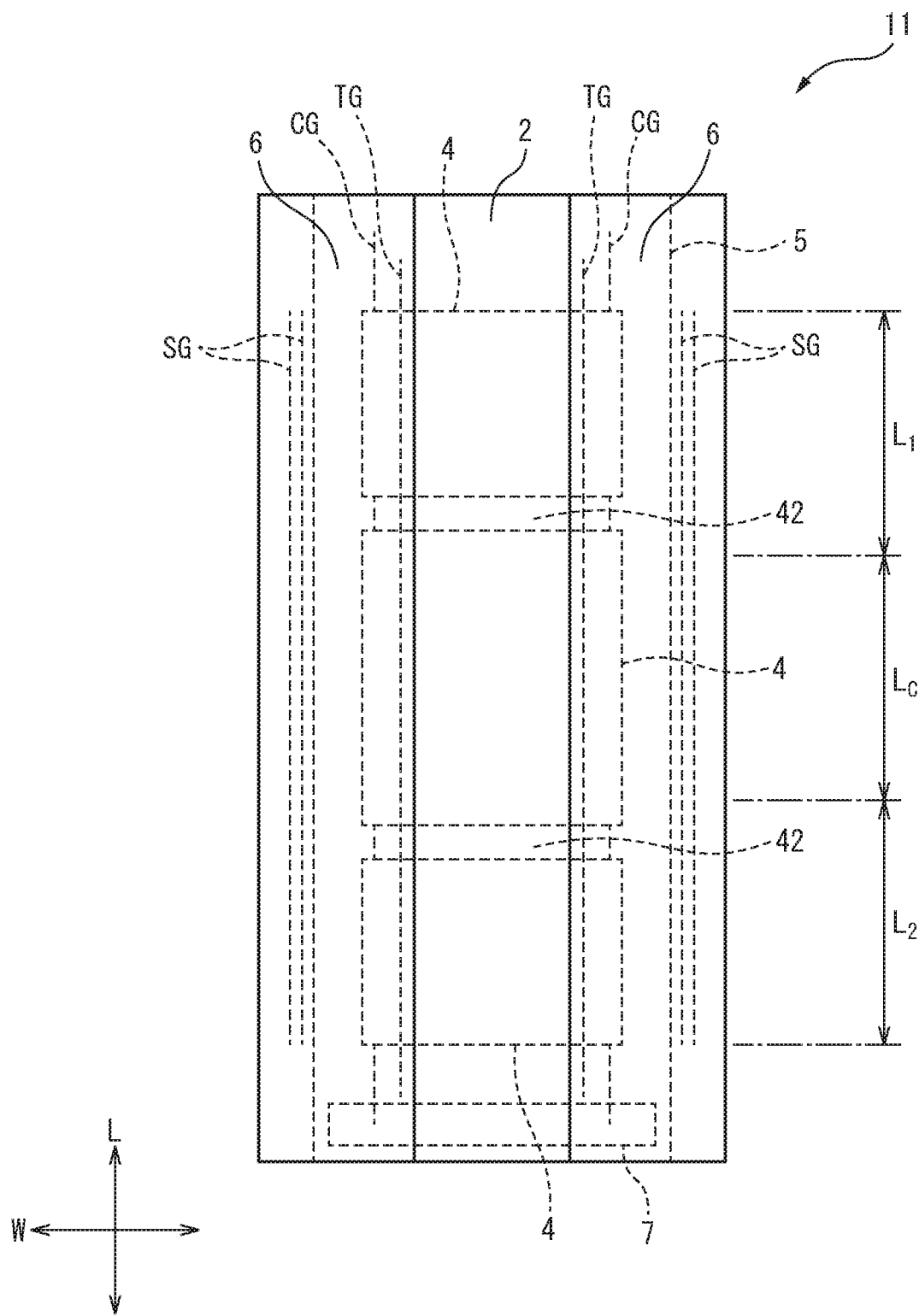
FIG. 8 is a plan view of the expanded state of a diaper for a pet 11 according to a third embodiment of the invention.

FIG. 8 is a plan view of the expanded state of a diaper for a pet 11 according to a third embodiment of the invention. In the diaper for a pet 11 of the third embodiment, as shown in FIG. 8, the absorbent body 4 has a lengthwise first region $L_1$, a lengthwise center region $L_C$ and a lengthwise second region $L_2$ in that order, that divide the absorbent body 4 into three equal portions in the lengthwise direction L in the plan view, and the deformation guide parts each formed by one slit 42 extending in the widthwise direction W of the diaper for a pet 11 are situated in the lengthwise first region $L_1$ and the lengthwise second region $L_2$, respectively. The one slit 42 forming each deformation guide part runs through the absorbent body 4 in the thickness direction T, and extends from one edge across to the other edge in the widthwise direction W of the absorbent body 4. Therefore, the absorbent body 4 is disposed inside the diaper for a pet 11, in a state divided into three sections in the lengthwise direction L by the slits 42 situated in the respective regions, the lengthwise first region $L_1$ and the lengthwise second region $L_2$.

For the third embodiment, the deformation guide parts are situated in the lengthwise first region $L_1$ and lengthwise second region $L_2$, but according to the invention there is no limitation to such an arrangement, and the deformation guide parts may instead be situated only on one or the other of the lengthwise first region $L_1$ and lengthwise second region $L_2$. If the deformation guide parts of the absorbent body 4 are thus situated in at least one of the lengthwise first region $L_1$ and lengthwise second region $L_2$, then when the diaper for a pet 11 is fitted onto the torso of the pet, the diaper for a pet 11 will run along the torso of the pet while allowing one end to be engaged and fastened at the proper position by the engagement section 7 situated at one end in the lengthwise direction L of the diaper for a pet 11. In addition, after the diaper for a pet 11 has been fitted onto the torso of the pet, the absorbent body 4 will be less likely to return from the state in which it is bent along the torso of the pet, to its original state (that is, the absorbent body 4 will be less likely to deform in a direction separating from the torso of the pet), and therefore the aforementioned engaged and fastened state can be easily maintained, and it will be less likely for gaps to form between the diaper for a pet 11 and the torso of the pet, or for the diaper for a pet 11 to shift from the proper wearing position.

Fourth Embodiment

Figure 9:
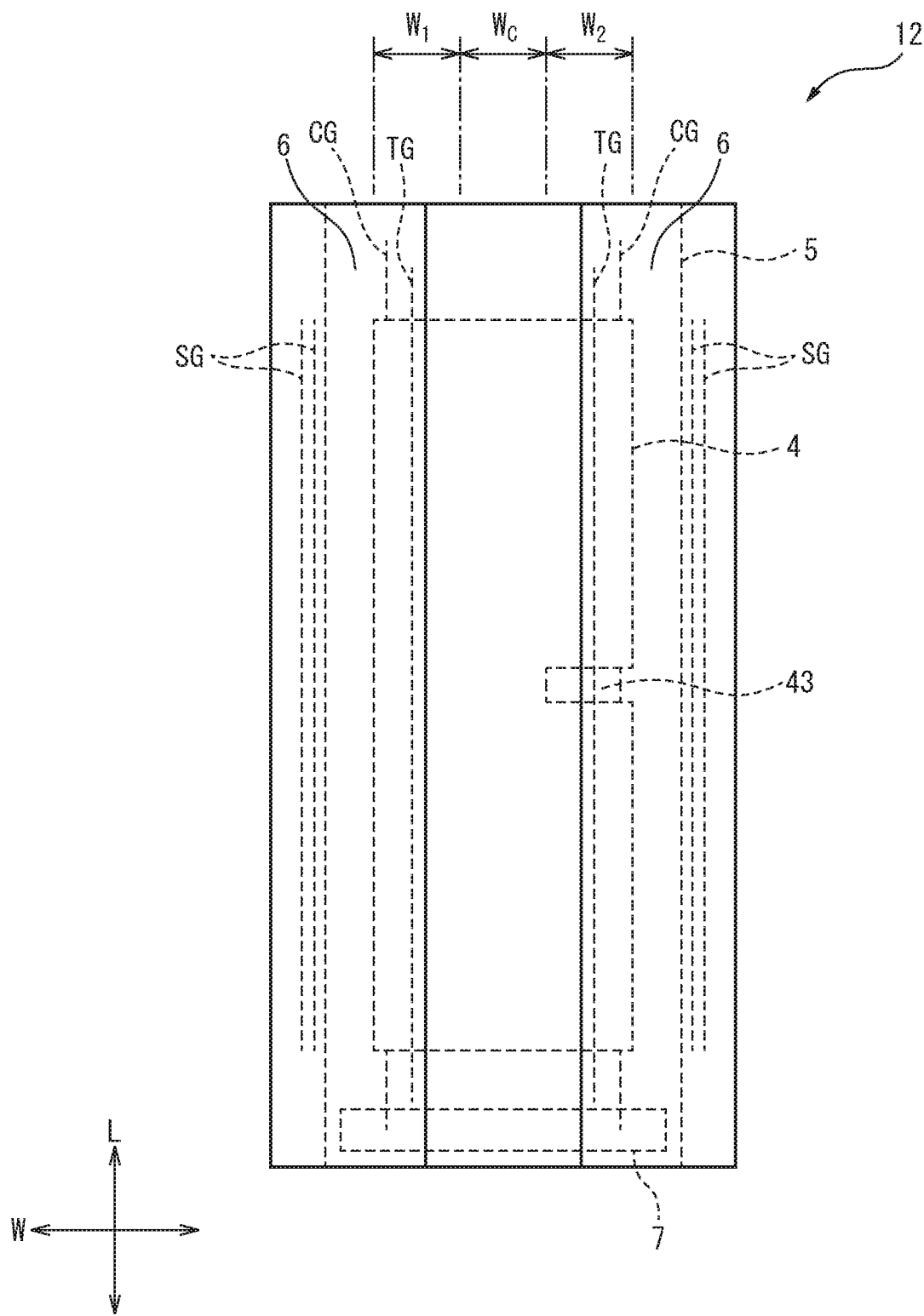
FIG. 9 is a plan view of the expanded state of a diaper for a pet 12 according to a fourth embodiment of the invention.

FIG. 9 is a plan view of the expanded state of a diaper for a pet 12 according to a fourth embodiment of the invention. In the diaper for a pet 12 of the fourth embodiment, as shown in FIG. 9, the absorbent body 4 has a widthwise first region $W_1$, a widthwise center region and $W_c$ and a widthwise second region $W_2$ in that order, that divide the absorbent body 4 into three equal portions in the widthwise direction W in the plan view, with the deformation guide part formed by a single slit 43, extending at a prescribed length in the widthwise direction W of the diaper for a pet 12, being situated in the widthwise second region $W_2$. The slit 43 forming the deformation guide part runs through the absorbent body 4 in the thickness direction T, and extends from one end across to the other end in the widthwise direction W in the widthwise second region $W_2$ of the absorbent body 4. Therefore, as shown in FIG. 9, the absorbent body 4 is disposed inside the diaper for a pet 12 in a state with the edge in the widthwise direction W running in the lengthwise direction L being partially notched by the slit 43 situated in the widthwise second region $W_2$.

For the fourth embodiment, the deformation guide part is situated in the widthwise second region $W_2$, but according to the invention there is no limitation to such an arrangement, and the deformation guide part may instead be situated in only the widthwise first region $W_1$, or in both the widthwise first region $W_1$ and the widthwise second region $W_2$. If the deformation guide part of the absorbent body 4 is thus situated in either or both the widthwise first region $W_1$ and widthwise second region $W_2$, then the diaper for a pet 12 can be easily deformed to match the body shape of the pet or changes in the torso dimension that occur with movement such as respiration by the pet. That is, if the deformation guide part of the absorbent body 4 is provided in the aforementioned region in the widthwise direction W (for example, the widthwise second region $W_2$) which is on the rear side (the gluteal region side) of the pet when the diaper for a pet 12 has been fitted onto the torso of the pet, then when the diaper for a pet 12 is fitted onto the torso of the pet, the diaper for a pet 12 can easily be accurately fitted to match the torso of the pet, conforming to the torso dimension that differs in the front-rear direction of the pet (that is, the widthwise direction W of the diaper for a pet 12) due to the body shape of the pet. On the other hand, if the deformation guide part of the absorbent body 4 is provided in a region in the widthwise direction W that is to be the front side (i.e. the head side) of the pet when the diaper for a pet 12 has been fitted onto the torso of the pet (for example, the widthwise first region $W_1$), then when the diaper for a pet 12 is fitted onto the torso of the pet, the absorbent body 4, and therefore the diaper for a pet 12, can deform following changes in the torso dimension in the front-rear direction of the pet caused by movement such as respiration by the pet, and the diaper for a pet 12 can satisfactorily maintain the closely fitted state onto the torso of the pet.

As a result, the diaper for a pet 12 according to the fourth embodiment will have excellent fittability with the torso of the pet and will be even less likely to shift from the proper wearing position (particularly in the front-rear direction of the pet). Particularly when the deformation guide part is situated at least in the lengthwise center region $L_C$, the deformation guide part of the absorbent body 4 can be situated to match the tip section of the excretory part of a male pet, so that when the diaper for a pet 12 is fitted onto the torso of the pet, the locations of the absorbent body 4 and the excretory part of the pet are even less likely to shift in the direction around the torso of the pet, and liquid excreta discharged from the pet can be even more accurately absorbed.

According to FIG. 9, incidentally, the deformation guide part of the fourth embodiment is situated in a region where the lengthwise center region $L_C$ overlaps with the widthwise second region $W_2$ of the absorbent body 4 in the plan view, but according to the invention the deformation guide part of the absorbent body may instead be situated in a region where either or both the lengthwise first region and lengthwise second region overlap with either or both the widthwise first region and widthwise second region. If the deformation guide part is situated in such a region, it will be possible to obtain the combined effects exhibited by having the deformation guide part situated in each of those regions.

Fifth Embodiment

Figure 10:
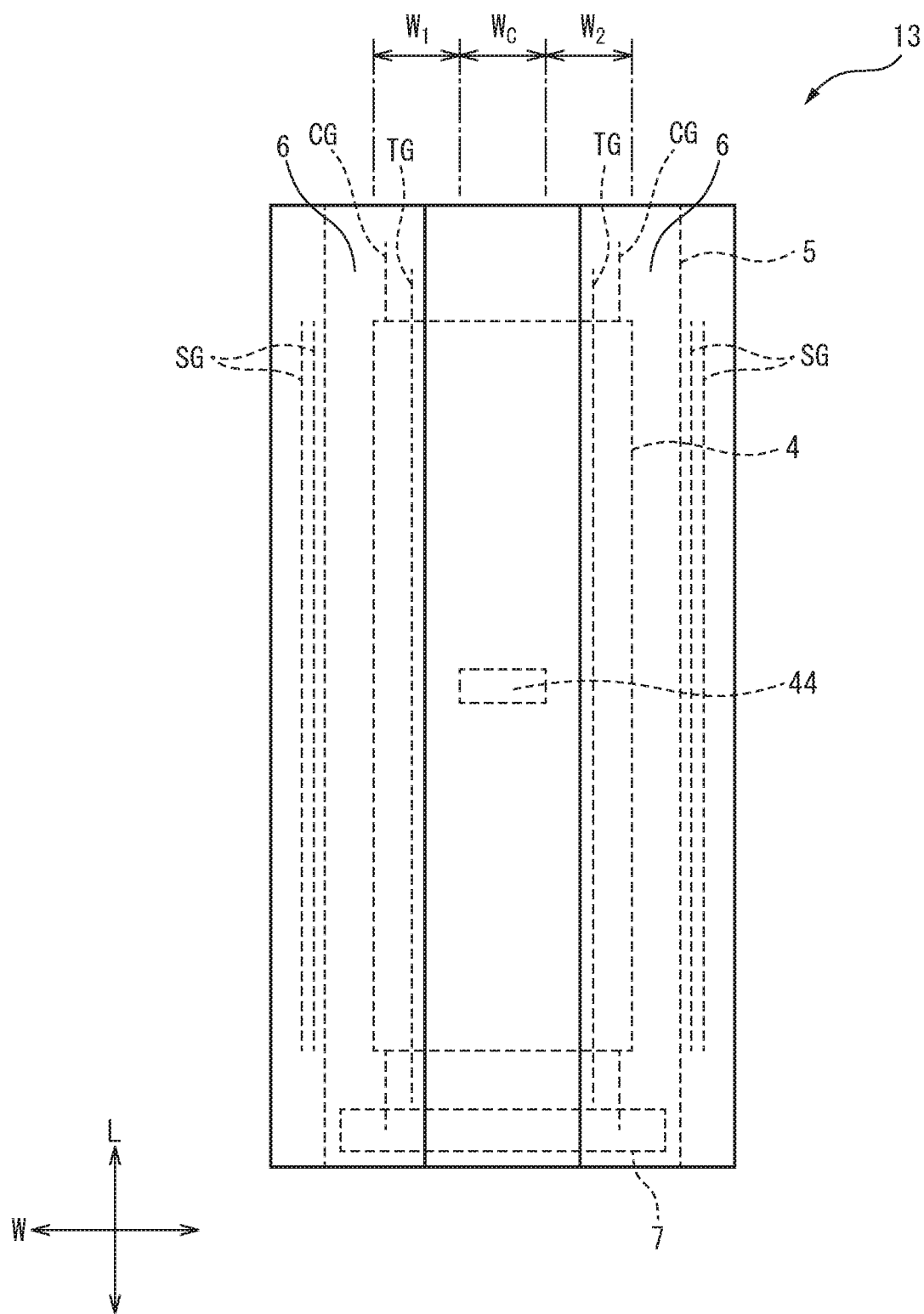
FIG. 10 is a plan view of the expanded state of a diaper for a pet 13 according to a fifth embodiment of the invention.

FIG. 10 is a plan view of the expanded state of a diaper for a pet 13 according to a fifth embodiment of the invention. In the diaper for a pet 13 of the fifth embodiment, as shown in FIG. 10, the absorbent body 4 has a widthwise first region $W_1$, a widthwise center region and $W_c$ and a widthwise second region $W_2$ in that order, that divide the absorbent body 4 into three equal portions in the widthwise direction W in the plan view, with the deformation guide part formed by a single slit 44, extending at a prescribed length in the widthwise direction W of the diaper for a pet 13, being situated in the widthwise center region $W_c$. The slit 44 forming the deformation guide part runs through the absorbent body 4 in the thickness direction T, and extends from one end across to the other end in the widthwise direction W in the widthwise center region $W_c$ of the absorbent body 4. Therefore, as shown in FIG. 10, the absorbent body 4 is disposed inside the diaper for a pet 13 in a state with the widthwise center region $W_c$ that runs in the lengthwise direction L being partially notched by the slit 43 situated in the widthwise center region $W_c$.

If the deformation guide part of the absorbent body 4 is situated in the widthwise center region $W_c$, then the diaper for a pet 13 will easily bend to a convex shape toward the non-torso-facing side Db in the widthwise center region $W_c$, allowing the aforementioned excreta-accommodating space to be formed locally between the diaper for a pet 13 and the torso of the pet. This allows the diaper for a pet 13 to hold liquid excreta in the excreta-accommodating space even when the pet has discharged a large amount of liquid excreta, thus more reliably preventing leakage of liquid excreta. In addition, if the deformation guide part of the absorbent body 4 is disposed in the widthwise center region $W_c$, the deformation guide part of the widthwise center region $W_c$ constitutes a bending origin, and the diaper for a pet 13 easily bends in the widthwise direction W to a convex shape toward the non-torso-facing side Db, so that the widthwise first region $W_1$ and widthwise second region $W_2$ can more easily fit in a close manner to the torso of the pet.

As a result, the diaper for a pet 13 of the fifth embodiment can more reliably prevent leakage of liquid excreta discharged from the pet, while also being even less likely to shift from the proper wearing position.

Incidentally, according to the fifth embodiment, the deformation guide part is situated in a region where the lengthwise center region $L_C$ and widthwise center region $W_c$ of the absorbent body 4 overlap, but the invention is not limited to such an arrangement, and the deformation guide part may instead be situated in a region where the widthwise center region overlaps with at least one from among the lengthwise first region, lengthwise center region and lengthwise second region. If the deformation guide part is situated in such a manner, it will be possible to obtain the combined effects exhibited by having the deformation guide part situated in each of those regions.

The construction of and the means for forming the deformation guide part in the absorbent body of the absorbent article for pets of the invention will now be described.

For each of the embodiments, the deformation guide part runs through the absorbent body 4 in the thickness direction T and is formed by a slit extending through at least a portion of the absorbent body 4 in the widthwise direction W, but according to the invention there is no limitation to such a slit, and any desired construction may be employed that allows deformation of the absorbent body to be guided. For example, the deformation guide part may be constructed by forming the absorbent body so that at least one of the neighboring regions among the two neighboring regions adjacent to both sides of the deformation guide part in the direction in which the deformation guide part extends, in the plan view, has a different rigidity than the deformation guide part (that is, by utilizing the difference in rigidity between a prescribed section of the absorbent body (the deformation guide part) and the surrounding section (neighboring region)).

The construction of the absorbent body such that the deformation guide part and its neighboring region has different rigidity is not particularly restricted, and for example, it may be (1) a construction wherein the basis weight of the absorbent body at the neighboring region is higher or lower than the basis weight of the absorbent body in the deformation guide part, (2) a construction wherein the density of the absorbent body in the neighboring region is higher or lower than the density of the absorbent body in the deformation guide part, or (3) a construction wherein the thickness of the absorbent body in the neighboring region is larger or smaller than the thickness of the absorbent body in the deformation guide part. Such a construction for the absorbent body can be realized by any method known in the relevant field, such as embossing, or content adjustment or notching of the absorbent material that is to form the absorbent body. Incidentally, for each of the embodiments, the absorbent body provided with a deformation guide part formed by a slit is included in the absorbent body construction of (1) above.

If the absorbent body is thus constructed so as to have different rigidity for the deformation guide part that extends in a direction intersecting with the lengthwise direction of the absorbent article for pets and for at least one of the neighboring regions of the two neighboring regions adjacent to both sides in the direction in which the deformation guide part extends, then the absorbent body will more easily bend in the lengthwise direction L (that is, in the direction corresponding to the direction around the torso of the pet when the absorbent article for pets is worn, with the border sections of different rigidity as bending origins, and therefore the absorbent body can ensure the function of the deformation guide part while also ensuring consistent absorption performance. Thus, the absorbent article for pets including the absorbent body can ensure excellent fittability with the torso of the pet, and can more accurately absorb liquid excreta such as urine.

Moreover, since the absorbent article for pets including such an absorbent body allows construction of the deformation guide part by forming a difference in rigidity in the absorbent body, an advantage is provided in that the ease of deformation, the direction of deformation and the manner of deformation of the deformation guide part can be easily controlled, and more accurate fittability can be exhibited to match the body shape of the pet.

Center Section Elastic Member

The center section elastic member that may be employed in the absorbent article for pets of the invention will now be described using the diaper for a pet 1 of the first embodiment.

In the diaper for a pet 1 of the first embodiment, as shown in FIG. 2 and FIG. 3, the center section elastic members CG are elastic members constructed of freely stretchable elastic yarns extending in the lengthwise direction L, and they are respectively disposed between the back sheet 3 and the absorbent body 4 at locations overlapping in the thickness direction T with both edges of the absorbent body 4 in the widthwise direction W, and impart contractive force in the lengthwise direction L of the diaper for a pet 1.

If the center section elastic members CG are disposed between the back sheet 3 and absorbent body 4 in this manner, then even when the absorbent body 4 has absorbed liquid excreta and swelled when the diaper for a pet 1 is being worn, the center section elastic members CG can impart contractive force so as to cover the swelled absorbent body 4 from the outer side (that is, the back sheet 3 side), and therefore the closely fitted state of the diaper for a pet 1 to the torso of the pet can be more reliably ensured. The diaper for a pet 1 can therefore accurately fit to the torso of the pet and be less likely to shift from the proper wearing position, even when the absorbent body 4 has absorbed a fixed amount of liquid excreta.

Moreover, if the center section elastic members CG are disposed between the back sheet 3 and absorbent body 4, then when an owner fits the diaper for a pet 1 onto a pet, the diaper for a pet 1 will deform to a convex shape on the top sheet 2 side (that is, toward the torso-facing side Da) and the deformation guide part will be easily visible through the top sheet 2, thus providing an advantage in that the owner can use the deformation guide part as a mark to easily fit the diaper for a pet 1 to the proper position.

Incidentally, the manner in which the center section elastic members are arranged in the absorbent article for pets of the invention is not limited to the first embodiment, so long as they extend in a direction intersecting with the widthwise direction of the absorbent article for pets and are disposed at locations overlapping with the absorbent body in the thickness direction, and they may be arranged at any desired locations, depending on the type and body frame of the pet. If the center section elastic members extend in a direction intersecting with the widthwise direction of the absorbent article for pets and are disposed at locations overlapping with the absorbent body in the thickness direction, then both edges of the absorbent article for pets in the lengthwise direction will be pulled by contractive force of the center section elastic members, resulting in easier fitting along the torso of the pet, and even when the torso dimensions change due to movement such as respiration by the pet, the absorbent article for pets will be able to match changes in the torso dimension to maintain a closely fitted state with the torso of the pet, making it even more unlikely that a gap will form between the absorbent article for pets and the torso of the pet or that the absorbent article for pets will shift from the proper wearing position.

In the absorbent article for pets of the invention, the center section elastic members may also be disposed between the top sheet and the absorbent body. Such an arrangement of the center section elastic members will now be described using the diaper for a pet 14 of the sixth embodiment of the invention.

Figure 11:
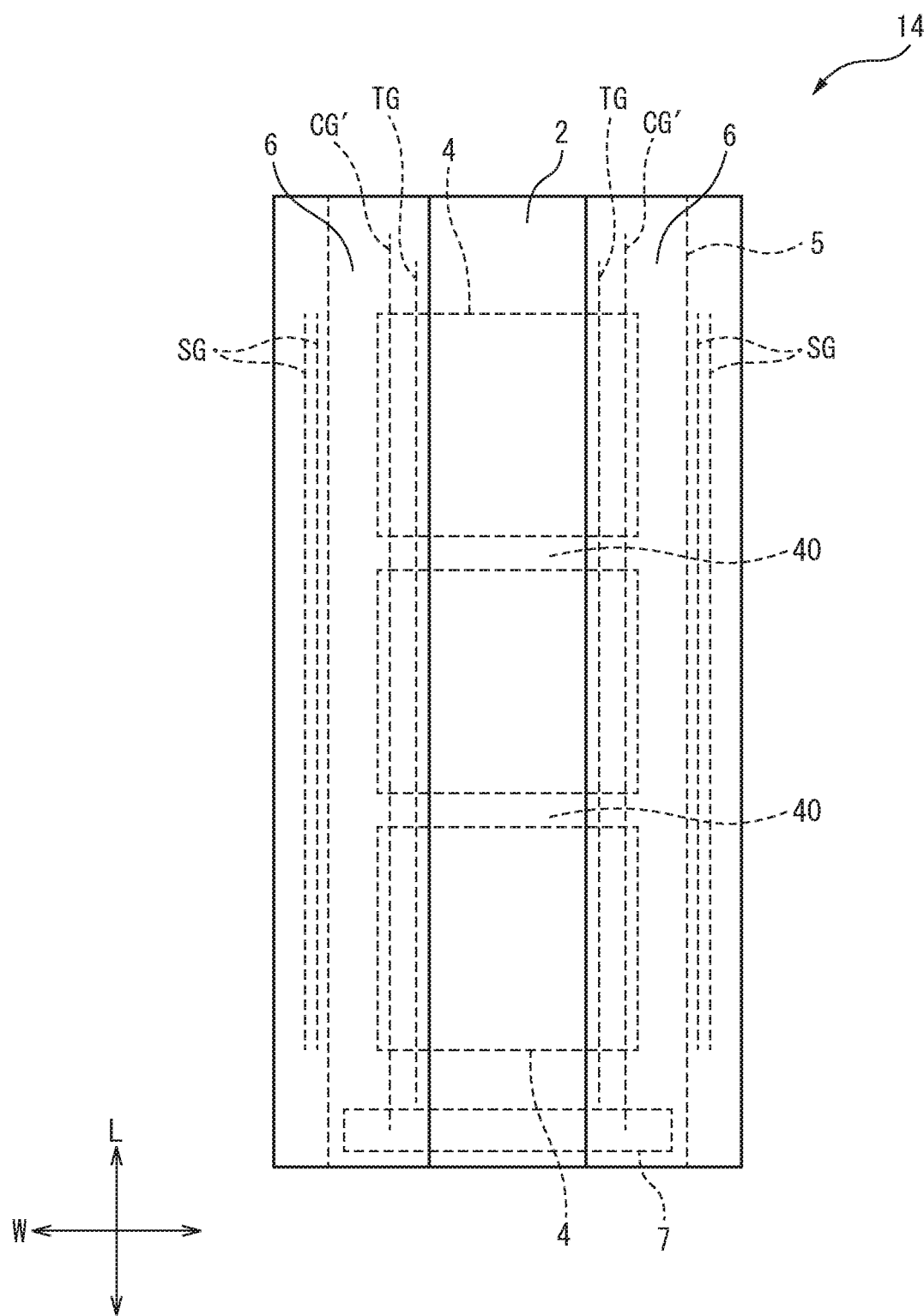
FIG. 11 is a plan view of the expanded state of a diaper for a pet 14 according to a sixth embodiment of the invention.

FIG. 11 is a plan view of the expanded state of a diaper for a pet 14 according to the sixth embodiment of the invention. The diaper for a pet 14 of the sixth embodiment has the same construction as the diaper for a pet 1 of the first embodiment, except that the pair of center section elastic members CG' running in the lengthwise direction L are disposed between the top sheet 2 and the absorbent body 4.

In the diaper for a pet 14 of the sixth embodiment, as shown in FIG. 11, the center section elastic members CG' are elastic members constructed of freely stretchable elastic yarns extending in the lengthwise direction L, and they are respectively disposed between the top sheet 2 and the absorbent body 4 at locations overlapping in the thickness direction T with both edges of the absorbent body 4 in the widthwise direction W, and impart contractive force in the lengthwise direction L of the diaper for a pet 14.

If the center section elastic members CG' are thus disposed between the top sheet 2 and the absorbent body 4, then the diaper for a pet 14 will easily shrink to wrap around the torso of the pet by contractive force of the center section elastic members CG' and more satisfactory fittability can be obtained when it is worn, thus making it even more unlikely that a gap will form between the diaper for a pet 14 and the torso of the pet or that the diaper for a pet 14 will shift from the proper wearing position.

Moreover, if the center section elastic members CG' are disposed between the top sheet 2 and absorbent body 4, another advantage is provided since the center section elastic members CG' will be easily visible through the top sheet 2, and therefore when the owner fits the diaper for a pet 14 onto the pet, it can be easily fitted to the proper position using the center section elastic members CG' as marks.

According to the invention, incidentally, the number of center section elastic members disposed at locations overlapping with the absorbent body in the thickness direction is not limited to those of each of the embodiments so long as the effect of the invention is not inhibited, and for example, one, two or more center section elastic members may be disposed only at locations overlapping in the thickness direction with only one of the two ends in the widthwise direction of the absorbent body, or one, two or more may be disposed at locations overlapping in the thickness direction with both ends in the widthwise direction of the absorbent body, depending on the type and body frame of the pet.

According to the invention, the center section elastic members are not particularly restricted so long as they are members that impart contractive force in the lengthwise direction to the absorbent article for pets in the expanded state, and for example, any elastic members such as rubber threads or flat rubber made of natural rubber; or filamentous or belt-shaped stretchable molded thermoplastic elastomers such as urethane or ethylene-vinyl acetate copolymer (EVA); or stretchable sheet members such as stretchable nonwoven fabrics, may be used.

Side Section Elastic Members

The side section elastic members that may be employed in the absorbent article for pets of the invention will now be described using the diaper for a pet 1 of the first embodiment.

In the diaper for a pet 1 of the first embodiment, as shown in FIG. 2 and FIG. 3, the side section elastic members SG are elastic members constructed of two freely stretchable elastic yarns each (that is, a total of 4 elastic yarns inside the diaper for a pet 1) extending in the lengthwise direction L, and they are respectively disposed between the side sheets 6 and the back sheet 3, at locations on both ends in the widthwise direction W of the diaper for a pet 1 (more specifically, the outer sides in the widthwise direction of the absorbent body 4), and impart contractive force in the lengthwise direction L of the diaper for a pet 1.

If the side section elastic members SG are respectively disposed at both ends in the widthwise direction W of the diaper for a pet 1, then when the diaper for a pet 1 is worn, deformation of the deformation guide part can be aided by contractive force of the side section elastic members SG, and both ends in the widthwise direction W of the diaper for a pet 1 (that is, the front-rear direction of the pet when it is worn) can be more accurately fitted along the torso of the pet, thus allowing leakage of liquid excreta discharged from the pet to be even more reliably prevented.

According to the invention, incidentally, the number of side section elastic members disposed at both ends in the widthwise direction of the absorbent article for pets is not limited to those of each of the embodiments so long as the effect of the invention is not inhibited, and for example, one, two or more side section elastic members may be disposed only at one end of both ends of the absorbent article for pets in the widthwise direction, or alternatively one each, or three or more each, may be disposed at locations of each of both ends of the absorbent article for pets in the widthwise direction, depending on the type and body frame of the pet.

According to the invention, the side section elastic members are not particularly restricted so long as they are members that can impart contractive force in the lengthwise direction of the absorbent article for pets in the expanded state, and any elastic members may be used, similar to the center section elastic members described above.

Surface-Section Elastic Members

Surface-section elastic members that may be employed in the absorbent article for pets of the invention will now be described using the diaper for a pet 1 of the first embodiment.

In the diaper for a pet 1 of the first embodiment, as shown in FIG. 2 and FIG. 3, the surface-section elastic members TG are elastic members constructed of a pair of freely stretchable elastic yarns extending in the lengthwise direction L, and they are respectively disposed at the inner side ends in the widthwise direction W of the pair of side sheets 6 located on the torso-facing side Da of the top sheet 2, and impart contractive force to the diaper for a pet 1 in the lengthwise direction L while causing the inner side ends (free ends) of the pair of side sheets 6 in the widthwise direction W to stand up on the torso-facing side Da of the top sheet 2, to form three-dimensional gathers as anti-leakage walls.

For the first embodiment, incidentally, as shown in FIG. 3, the surface-section elastic members TG are constructed of filamentous elastic yarns and are disposed so as to cause the inner side ends in the widthwise direction W of the pair of side sheets 6 to stand up on the torso-facing side Da of the top sheet 2 and form three-dimensional gathers, but the invention is not limited to such an aspect, and instead the surface-section elastic members may be constructed of belt-shaped hydrophobic elastic members having prescribed widthwise lengths, and being joined to the torso-facing surface of the back sheet or top sheet so that the belt-shaped hydrophobic elastic members themselves stand up to form anti-leakage walls on the torso-facing side of the top sheet.

If such surface-section elastic members TG are disposed further on the torso-facing side Da than the top sheet 2, then contractive force of the surface-section elastic members TG will be able to aid deformation of the deformation guide parts, and facilitate formation of anti-leakage walls running in the lengthwise direction L between the top sheet 2 and torso of the pet, thus allowing leakage of liquid excreta discharged from the pet to be more reliably prevented.

According to the invention, incidentally, the number of surface-section elastic members disposed on the torso-facing side of the top sheet is not limited to the embodiments described above so long as the effect of the invention is not inhibited, and for example, one, two or more surface-section elastic members may be disposed on both sides of the widthwise center axis line running in the lengthwise direction of the absorbent article for pets, or one, two or more may be disposed only on one side of the widthwise center axis line running in the lengthwise direction, depending on the type and body frame of the pet.

According to the invention, the surface-section elastic members are not particularly restricted so long as they are members that impart contractive force in the lengthwise direction of the absorbent article for pets in the expanded state and can form anti-leakage walls on the torso-facing side of the top sheet, and any desired elastic members, similar to the center section elastic members may be used.

Side Sheets

The side sheets that may be employed in the absorbent article for pets of the invention will now be described using the diaper for a pet 1 of the first embodiment.

In the diaper for a pet 1 of the first embodiment, as shown in FIGS. 1 to 3, the pair of side sheets 6 are each constructed of belt-shaped hydrophobic sheet members that are long in the lengthwise direction L in the plan view, and they are disposed on both sides of the widthwise center axis line (not shown) running in the lengthwise direction L of the diaper for a pet 1, on the torso-facing side Da of the top sheet 2. In each of the pair of side sheets 6, the non-torso-facing surfaces at the ends located on the outer sides in the widthwise direction W and running in the lengthwise direction L (hereunder referred to as "outer side ends in the widthwise direction W"), and the non-torso-facing surfaces at both ends in the lengthwise direction L, are each joined with the torso-facing surface of the back sheet 3, while the non-torso-facing surface at the ends located on the inner sides in the widthwise direction W and running in the lengthwise direction L (hereunder referred to as "inner side ends in the widthwise direction W") is not joined with either of the sheet members (for example, the top sheet or back sheet). Therefore, as shown in FIG. 1 and FIG. 3, the pair of side sheets 6 have the outer side ends in the widthwise direction W as fixed ends and the inner side ends in the widthwise direction W as free ends.

Also, as shown in FIG. 3, each of the inner side ends in the widthwise direction W of the pair of side sheets 6 is folded toward the top sheet 2 side, and the surface-section elastic members TG running in the lengthwise direction L are disposed in a manner enveloped by the folded ends. Contraction of the surface-section elastic members TG causes the inner side ends in the widthwise direction W (free ends) of the pair of side sheets 6 to rise from the top sheet 2 side, allowing formation of three-dimensional gathers, as shown in FIG. 1 and FIG. 3. In the diaper for a pet 1 of the first embodiment, such three-dimensional gathers function as anti-leakage walls, such that liquid excreta such as urine that have been discharged from the pet are even less likely to leak.

The side sheets that may be employed in the absorbent article for pets of the invention are not particularly restricted so long as they can function as anti-leakage walls when forming three-dimensional gathers, and for example, they may each be constructed of any water-repellent or hydrophobic nonwoven fabric (for example, a spunlace nonwoven fabric, spunbond nonwoven fabric, thermal bonded nonwoven fabric, meltblown nonwoven fabric or air-through nonwoven fabric). Moreover, the fibers composing the nonwoven fabric are not particularly restricted, and for example, synthetic fibers such as polyolefin-based fibers, polyester-based fibers or polyamide-based fibers, or cellulosic fibers such as rayon or cotton, may be used.

Engagement Section

The engagement section that may be employed in the absorbent article for pets of the invention will now be described using the diaper for a pet 1 of the first embodiment.

As shown in FIG. 1, FIG. 2 and FIG. 4, the engagement section 7 in the diaper for a pet 1 of the first embodiment is disposed at one end in the lengthwise direction L of the diaper for a pet 1, on the non-torso-facing surface of the back sheet 3, and it has an essentially rectangular outer shape horizontally, running in the widthwise direction W of the diaper for a pet 1. As shown in FIG. 4, the engagement section 7 is constructed of a mechanical fastener comprising a belt-shaped base joined to the non-torso-facing surface of the back sheet 3 and a plurality of hook members protruding from the base to the non-torso-facing side Db, and since the mechanical fastener has a plurality of hook members that are able to engage with any fiber structure such as a nonwoven fabric, when the diaper for a pet 1 is fitted along the torso from the abdominal region side of the pet, the hook members can be engaged with any portion of the torso-facing surface of the top sheet 2 on the dorsal region side of the pet. By having such an engagement section 7, the diaper for a pet 1 can be accurately fitted at the proper location of the torso of the pet, matching the dimensions of the torso of the pet.

According to the invention, incidentally, the form of the engagement section is not limited to the specific mechanical fastener described above, and the engagement section may employ any surface fastener, such as a mechanical fastener composed of hook members and loop members, for example.

According to the invention, the location where the engagement section is disposed is not limited to the location for the embodiments described above, and instead the engagement section may be disposed at one end in the lengthwise direction of the absorbent article for pets on the torso-facing surface of the top sheet, or it may be disposed at one end in the lengthwise direction on the torso-facing surface of the top sheet and at the other end in the lengthwise direction on the non-torso-facing surface of the back sheet.

Back Film

The back film that may be employed in the absorbent article for pets of the invention will now be described using the diaper for a pet 1 of the first embodiment.

As shown in FIGS. 2 to 4, the back film 5 of the diaper for a pet 1 of the first embodiment has a longitudinal rectangular outer shape extending in the lengthwise direction L and widthwise direction W of the diaper for a pet 1, in the plan view, and it is composed of a liquid-impermeable film that is disposed between the absorbent body 4 and back sheet 3 and that, together with the back sheet, prevents leakage of liquid excreta such as urine that have permeated the top sheet 2 or absorbent body 4. The back film 5 may be constructed of the same liquid-impermeable sheet member as the back sheet 3 described above, and for example, it may be constructed of a hydrophobic nonwoven fabric, SMS layered nonwoven fabric, liquid-impermeable plastic film, or a laminated sheet comprising any desired combination of these sheets.

The method of producing the absorbent article for pets of the invention using the members described above is not particularly restricted, and any method known in the relevant field may be used. For example, the diaper for a pet 1 of the first embodiment of the invention may be produced by stacking the members that are to compose the diaper for a pet 1, i.e. the pair of side sheets 6 having surface-section elastic members TG disposed on the inner side ends in the widthwise direction W, the top sheet 2, the absorbent body 4 having slits 40 formed as deformation guide parts, the pair of center section elastic members CG, the back film 5, the pair of side section elastic members SG with two yarns each and the back sheet 3, as shown in FIG. 3 and FIG. 4, and joining them with any joining means. The means for joining the members is not particularly restricted, and any joining means may be employed such as a method of bonding with a hot-melt adhesive, a heat sealing method or an ultrasonic bonding method.

The present invention can be applied to a variety of absorbent articles for pets other than a disposable diaper for a pet according to the embodiments described above, such as a (light) incontinence pad for a pet, for example. Moreover, the absorbent article for pets of the invention is not limited to each of the embodiments described above, and it may incorporate appropriate combinations, substitutes and modifications within a range that is still within the object and gist of the invention. Incidentally, the ordinal terms "first" and "second" as used throughout the present specification serve merely to distinguish between the numbered embodiments and are not used to mean any relative ordering, precedence or importance.

REFERENCE SIGNS LIST

1 Diaper for a pet (absorbent article for pets)
2 Top sheet
3 Back sheet
4 Absorbent body
40 Slit (deformation guide part)
5 Back film
6 Side sheet
7 Engagement section
CG Center section elastic member
TG Surface-section elastic member
SG Side section elastic member

The invention claimed is:

1. An absorbent article for pets having a lengthwise direction, a widthwise direction and a thickness direction that are mutually perpendicular, and which is worn with the lengthwise direction extending around the torso of a pet,
the absorbent article for pets including an absorbent body provided with a deformation guide part that extends in a direction intersecting with the lengthwise direction, in a plan view; and an engagement section on at least one end of the article in the lengthwise direction engageable with an interior surface of the article at an opposite end of the article to form a cylindrical shape around the torso of a pet when the article is worn by the pet.

2. The absorbent article for pets according to claim 1, wherein the absorbent body has a lengthwise first region, a lengthwise center region and a lengthwise second region in that order, that divide the absorbent body into three equal portions in the lengthwise direction in the plan view, the deformation guide part being disposed at least in the lengthwise center region.

3. The absorbent article for pets according to claim 2, wherein the absorbent body has a widthwise first region, a widthwise center region and a widthwise second region in that order, that divide the absorbent body into three equal portions in the widthwise direction in the plan view, the deformation guide part being disposed in the widthwise center region of the absorbent body.

4. The absorbent article for pets according to claim 1, wherein
the absorbent article for pets comprises an engagement section on at least one end in the lengthwise direction, and
the absorbent body has a lengthwise first region, a lengthwise center region and a lengthwise second region in that order, that divide the absorbent body into three equal portions in the lengthwise direction in the plan view, while the deformation guide part is disposed in either or both of the lengthwise first region and the lengthwise second region.

5. The absorbent article for pets according to claim 1, wherein the absorbent body has a widthwise first region, a widthwise center region and a widthwise second region in that order, that divide the absorbent body into three equal portions in the widthwise direction in the plan view, the deformation guide part being disposed in either or both of the widthwise first region and the widthwise second region.

6. The absorbent article for pets according to claim 1, wherein the absorbent article for pets comprises a freely stretchable center section elastic member extending in a direction intersecting with the widthwise direction and overlapping with the absorbent body in the thickness direction.

7. The absorbent article for pets according to claim 6, wherein
the absorbent article for pets comprises, in the thickness direction, a liquid-permeable top sheet, a liquid-impermeable back sheet and the absorbent body situated between these sheets, and
the center section elastic member is disposed between the top sheet and the absorbent body.

8. The absorbent article for pets according to claim 6, wherein
the absorbent article for pets comprises, in the thickness direction, a liquid-permeable top sheet, a liquid-impermeable back sheet and the absorbent body situated between these sheets, and
the center section elastic member is disposed between the back sheet and the absorbent body.

9. The absorbent article for pets according to claim 1, wherein the absorbent article for pets comprises freely stretchable side section elastic member extending in the lengthwise direction on each of both ends in the widthwise direction, in the plan view.

10. The absorbent article for pets according to claim 1, wherein
the absorbent article for pets has a torso-facing surface that faces the torso of the pet and a non-torso-facing surface on an opposite side from the torso-facing surface, when it is fitted onto the torso of the pet, and in the thickness direction, the absorbent article comprises a liquid-permeable top sheet, a liquid-impermeable back sheet, the absorbent body situated between these sheets, and a freely stretchable surface-section elastic member located further to the torso-facing side than the top sheet and extending in the lengthwise direction.

11. The absorbent article for pets according to claim 1, wherein the absorbent body has different rigidity for the deformation guide part and for at least one neighboring regions of two neighboring regions adjacent to both sides of the deformation guide part, in the direction in which the deformation guide part extends in the plan view.

* * * * *